United States Patent
Berger et al.

(10) Patent No.: US 10,117,809 B2
(45) Date of Patent: Nov. 6, 2018

(54) COMPOSITIONS FOR ENDODONTIC PROCEDURES

(71) Applicant: DENTSPLY SIRONA, Inc., York, PA (US)

(72) Inventors: Todd Berger, Owasso, OK (US); Kevin Wilkinson, Bixby, OK (US); Adam Baratz, Tulsa, OK (US); Dan Ammon, York, PA (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/139,959

(22) Filed: Apr. 27, 2016

(65) Prior Publication Data

US 2016/0235632 A1    Aug. 18, 2016

Related U.S. Application Data

(63) Continuation of application No. 13/942,446, filed on Jul. 15, 2013, now Pat. No. 9,351,909.

(60) Provisional application No. 61/671,251, filed on Jul. 13, 2012.

(51) Int. Cl.
| | | |
|---|---|---|
| *A61K 6/093* | (2006.01) | |
| *C08F 220/32* | (2006.01) | |
| *C08F 230/08* | (2006.01) | |
| *A61K 6/083* | (2006.01) | |
| *A61K 6/00* | (2006.01) | |
| *C07F 7/08* | (2006.01) | |
| *C08F 230/02* | (2006.01) | |
| *A61C 5/50* | (2017.01) | |

(52) U.S. Cl.
CPC .............. *A61K 6/083* (2013.01); *A61C 5/50* (2017.02); *A61K 6/0038* (2013.01); *A61K 6/0091* (2013.01); *A61K 6/093* (2013.01); *C07F 7/0849* (2013.01); *C08F 220/32* (2013.01); *C08F 230/02* (2013.01); *C08F 230/08* (2013.01); *C08F 2220/325* (2013.01); *C08F 2230/085* (2013.01)

(58) Field of Classification Search
None
See application file for complete search history.

(56) References Cited

U.S. PATENT DOCUMENTS

| | | | | |
|---|---|---|---|---|
| 4,380,432 A | * | 4/1983 | Orlowski | A61K 6/0088 433/180 |
| 4,722,689 A | * | 2/1988 | Corbett | A61C 13/0003 433/17 |
| 4,810,768 A | * | 3/1989 | Wong | C08K 5/09 528/12 |
| 4,822,687 A | * | 4/1989 | Kessel | C09D 183/06 428/447 |
| 4,894,011 A | * | 1/1990 | Johnson | A61O 5/50 433/81 |
| 5,078,988 A | * | 1/1992 | Lin | A61K 8/41 424/49 |
| 5,118,297 A | * | 6/1992 | Johnson | A61O 5/50 433/224 |
| 5,154,915 A | * | 10/1992 | Weber | A61K 8/43 424/49 |
| 5,189,077 A | * | 2/1993 | Kerby | A61K 6/0023 523/115 |
| 5,395,666 A | * | 3/1995 | Brindle | A61L 31/10 2/168 |
| 5,833,457 A | * | 11/1998 | Johnson | A61C 13/30 433/102 |
| 6,343,929 B1 | * | 2/2002 | Fischer | A61C 3/005 433/224 |
| 6,353,041 B1 | * | 3/2002 | Qian | A61K 6/0038 433/228.1 |
| 6,387,981 B1 | * | 5/2002 | Zhang | A61K 6/0017 522/81 |
| 6,403,751 B1 | * | 6/2002 | Engelbrecht | A61K 6/0017 528/25 |
| 6,407,148 B1 | * | 6/2002 | Krejci | A61K 6/0017 106/35 |
| 2002/0051952 A1 | * | 5/2002 | Kamohara | A61K 6/0038 433/228.1 |
| 2002/0088372 A1 | * | 7/2002 | Abiru | A61K 6/0038 106/35 |
| 2004/0048975 A1 | * | 3/2004 | Frances | A61K 6/093 524/588 |
| 2005/0260269 A1 | * | 11/2005 | Engelbrecht | A61K 6/0023 424/486 |
| 2008/0190322 A1 | * | 8/2008 | Chen | A41D 19/0058 106/218 |
| 2009/0326114 A1 | * | 12/2009 | Grothe | C08K 3/30 524/148 |
| 2010/0068679 A1 | * | 3/2010 | Zappini | A61K 6/0044 433/225 |
| 2011/0070563 A1 | * | 3/2011 | Ori | A61K 6/0038 433/224 |
| 2011/0230591 A1 | * | 9/2011 | Berger | A61O 5/50 523/117 |

* cited by examiner

*Primary Examiner* — Peter A Salamon
(74) *Attorney, Agent, or Firm* — Dentsply Sirona Inc.

(57) ABSTRACT

An adhesion promoter for endodontic sealant compositions for filling and sealing a root canal.

33 Claims, No Drawings

COMPOSITIONS FOR ENDODONTIC PROCEDURES

CROSS-REFERENCE TO RELATED APPLICATIONS

This application is a continuation application of U.S. application Ser. No. 13/942,446, filed Jul. 15, 2013, which claims the benefit of and priority to U.S. Provisional Patent Application Ser. No. 61/671,251, filed on Jul. 13, 2012, which are herein incorporated by reference for all purposes.

FIELD OF THE INVENTION

The present invention is directed to a dental composition, and specifically to an improved composition for endodontic procedures useful for filling root canals.

BACKGROUND OF THE INVENTION

Previous root canals procedures included a step of sealing the root canal with a sealant material and then a step of filling the sealed root canal with a filling material. Most typical "sealers" are generally hydrocarbon based amine/epoxy systems, which may result in an unstable system when mixed with powder of a filling material such as ground up gutta-percha points.

Gutta-percha is the most widely used obturation material. However, gutta-percha does not create a seal. It is a second composition referred to as a sealer which creates the seal and then the two materials work together to prevent bacteria from entering the canal system. The gutta-percha can be improved by heating it above its melt temperature thus allowing it to flow. The melted gutta-percha is compacted with a heated a plugger or a solid carrier. The liquid gutta-percha flows into tubules carrying sealer along with it, thus, creating a more complete seal of the root canal system. However, heated gutta-percha has a very high viscosity and tends to be tacky. So, while it flows, it cannot penetrate all tubules or openings, thus the sealer cannot completely seal the entire system.

The gutta-percha can be improved by heating it above its melt temperature thus allowing it to flow. The melted gutta-percha is compacted with a heated a plugger or a solid carrier. The liquid gutta-percha flows into tubules carrying sealer along with it, thus, creating a more complete seal of the root canal system. However, heated gutta-percha has a very high viscosity and tends to be tacky. So, while it flows, it cannot penetrate all tubules or openings, thus the sealer cannot completely seal the entire system.

Since the sealer will be in the canal system in very thin layers it must be very radiopaque to be seen on the x-ray. Therefore, sealers are typically a reactive composite made up mostly of radiopacifier. If the sealer is to flow to fill the very small gaps to create the seal, the polymer portion of the composite must be a very low viscosity (low molecular weight).

Many sealer formulations have been used over the years, zinc oxide eugenol, epoxy amines and acrylates. All these two part systems are heavily filled liquids which once mixed form a paste and then later set into a solid. Sealers of this type cannot be used without the gutta-percha since they would be nearly impossible to retreat, have no method to compact them into the tubules and are not formulated to be used in thick layers.

Although these traditional gutta-percha sealer compositions are generally effective in treating root canals, it would be desirable to have a gutta-percha/sealer 2 in 1 composition which could fill the canal system without the need for heat. Ideally, the 2 in 1 composition would have a lower viscosity and be less tacky than melted gutta-percha. This improvement would increase the penetration of the composition into the complex of tubules and tiny openings to more completely seal the entire root canal system. More particularly, the present invention attempts to overcome these deficiencies by providing stable improved 2-in-1 sealer composition (e.g., a composite sealant composition) and/or adhesion promoter with optional cross-linked formulations and methods for treating root canals using compositions thereof. Desirably, the present invention provides such improved obturation compositions having these desirable properties as well as other beneficial features and advantages.

SUMMARY OF THE INVENTION

The present invention seeks to improve upon prior obturation systems and particularly the filling a tooth root canal.

In one aspect, the present invention contemplates an endodontic composite sealant composition for filling and sealing a root canal comprising: cross-linked-polyisoprene micro particles.

In another aspect, the present invention contemplates an endodontic composite sealant composition for filling and sealing a root canal comprising an adhesion promoter.

In another aspect, the present invention contemplates a method for sealing a root canal with a composite sealant composition comprising the steps of: providing a mixture including cis-polyisoprene, a cross-linker, an initiator, a filler, zinc oxide and radiopacifier; curing the mixture to form a cured cross-linked cis-polyisoprene material; grinding the cured cross-linked cis-polyisoprene material cryogenically to form microparticles; providing a first component mixture including an epoxy based polymerizable compound and at least one of a radiopacifier, a filler, and the cured cross-linked cis-polyisoprene microparticles; providing a second component mixture including an amine-based polymerizable compound, a curing agent and at least one of a radiopacifier, a filler, and the cured cross-linked cis-polyisoprene microparticles; and filling the root canal with the first component mixture and the second component mixture to form a cured composite sealant material; wherein the first component mixture, the second component mixture, or both include the cured cross-linked cis-polyisoprene microparticles.

In another aspect, the present invention contemplates An adhesion promoter comprising the following formula (I):
$R^1$—$R^2$—W—Z—$R^3$—$R^4$ (I) wherein

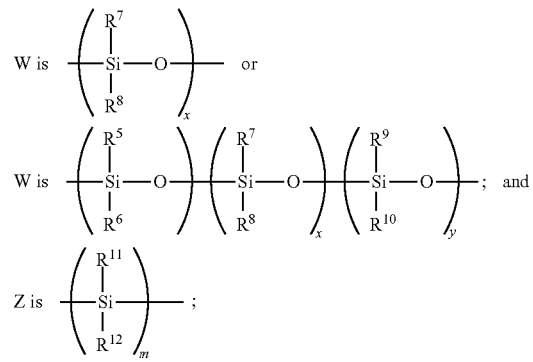

wherein $R^1$ and $R^4$ are independently Hydrogen, $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group; $R^2$ and $R^3$ are independently a $C_{1-10}$ alkyl group, $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group; $R^5$, $R^6$, $R^7$, $R^8$, $R^9$, $R^{10}$, $R^{11}$, and $R^{12}$ are independently Hydrogen, a $C_{1-10}$ alkyl group, or a $C_{1-10}$—$R^{13}$ group such that $R^{13}$ is independently $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group, whereas multiple groups of $R^5$, $R^6$, $R^7$, $R^8$, $R^9$, $R^{10}$, $R^{11}$, $R^{12}$, and $R^{13}$ may be identical or different; and x is an integer from 1 to 1000, multiple groups of x may be identical or different; y is an integer from 1 to 1000, multiple groups of y may be identical or different; and m is an integer from 1 to 1000, multiple groups of m may be identical or different.

In yet another aspect, any of the aspects of the present invention may be further characterized by one or any combination of the following features: the cross-linked-polyisoprene microparticles are synthesized from cis-polyisoprene; further comprising a polymerizable compound, a curing agent, and a filler; a portion of the polymerizable compound includes a ring-opening functionality, a reactive-cyclic functionality, a free radical functionality, or any combination thereof; the ring-opening functionality is selected from the group consisting of an acid group, an amine group, a thiol group and an alcohol group; the reactive-cyclic functionality is selected from the group consisting of an epoxy group, an anhydride group, an aziridine group and an oxazolone group; the free radical functionality is selected from the group consisting of a double bond and a triple bond; the adhesion promoter includes a dentin binding functionality; the dentin binding functionality includes a negative charge, a positive charge, an amphoteric charge, or a zwitterionic charge; the negative or positive charge comprises carboxylic acid groups, sulfate groups, amine groups, phosphate groups, quaternary ammonium groups and sulfonate, betaine, phosphatidylcholine groups; the cross-linked polyisoprene microparticles are less than about 200 μm; the cross-linked-cis-polyisoprene microparticles range from about 50 to about 180 μm; up to about 50% by weight is the cross-linked cis-polyisoprene powder, wherein the composition further comprises: up to about 80 weight % a radiopacifier selected from the group consisting of tungsten, zinc, zinc oxide, tungsten oxide, barium, barium sulfate, bismuth, bismuth oxide, and calcium tungstate; up to about 10% a curing agent, up to about 40% a filler, wherein the filler is a polymer, silica, cross-linked-cis-polyisoprene microparticles or fumed silica, or any combination thereof, and up to about 50% an adhesion promoter; the curing agent includes a catalyst having an amine group; the cross-linked-cis-polyisoprene microparticles comprises fibers, crosslinking agents, initiators, radiopacifiers, cis-polyisoprene, and/or antimicrobial agent; the initiator is selected from the group consisting of a free radical initiator or cationic initiator, and platinum initiator; the adhesion promoter is characterized by the following formula (I): $R^1$—$R^2$—W—Z—$R^3$—$R^4$ (I) wherein

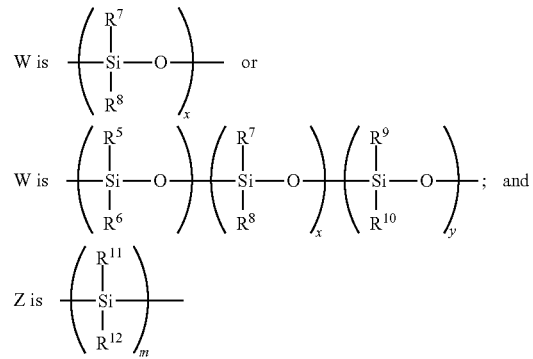

wherein $R^1$ and $R^4$ are independently Hydrogen, $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group; $R^2$ and $R^3$ are independently a $C_{1-10}$ alkyl group, $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group; $R^5$, $R^6$, $R^7$, $R^8$, $R^9$, $R^{10}$, $R^{11}$, and $R^{12}$ are independently Hydrogen, a $C_{1-10}$ alkyl group, or a $C_{1-10}$—$R^{13}$ group such that $R^{13}$ is independently $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group, whereas multiple groups of $R^5$, $R^6$, $R^7$, $R^8$, $R^9$, $R^{10}$, $R^{11}$, $R^{12}$, and $R^{13}$ may be identical or different; and x is an integer from 1 to 1000, multiple groups of x may be identical or different; y is an integer from 1 to 1000, multiple groups of y may be identical or different; and m is an integer from 1 to 1000, multiple groups of m may be identical or different; wherein i) $R^1$ and $R^4$ are independently an epoxide, a succunic anhydride, or a succinimide group; ii) $R^1$ and $R^4$ are independently $NH_2$, OH, COOH, or SH group; or iii) at least one of $R^1$ and $R^4$ is independently a phosphate, a sulfate, a sulfonate, a betaine, a carboxylic acid, an amino acid, a diacids, a bisphosphate, or a phosphatidylcholine group; wherein i) $R^1$ and $R^4$ are independently an epoxide, a succunic anhydride, or a succinimide group; and ii) at least one of $R^5$, $R^6$, $R^7$, $R^8$, $R^9$, $R^{10}$, $R^{11}$, and $R^{12}$ is independently the $C_{1-10}$—$R^{13}$ group such that $R^{13}$ is independently the phosphate, the sulfate, the sulfonate, the betaine, the carboxylic acid, the amino acid, the diacids, the bisphosphate, or the phosphatidylcholine group; wherein: i) $R^1$ and $R^4$ are independently $NH_2$, OH, COOH, or SH group; and ii) at least one of $R^5$, $R^6$, $R^7$, $R^8$, $R^9$, $R^{10}$, $R^{11}$, and $R^{12}$ is independently the $C_{1-10}$—$R^{13}$ group such that $R^{13}$ is independently the phosphate, the sulfate, the sulfonate, the betaine, the carboxylic acid, the amino acid, the diacids, the bisphosphate, or the phosphatidylcholine group; wherein: i) at least one of $R^1$ and $R^4$ is independently a phosphate, a sulfate, a sulfonate, a betaine, a carboxylic acid, an amino acid, a diacids, a bisphosphate, or a phosphatidylcholine group; and ii) at least one of $R^5$, $R^6$, $R^7$, $R^8$, $R^9$, $R^{10}$, $R^{11}$, and $R^{12}$ is independently the $C_{1-10}$—$R^{13}$ group such that $R^{13}$ is independently the $NH_2$, OH, COOH, SH, epoxide, succunic anhydride, or succinimide group, whereas $NH_2$, OH, COOH, or SH group is not present when the epoxide, the succunic anhydride, or the succinimide group is present; wherein $R^5$, $R^6$, $R^{11}$, and $R^{12}$ are independently a $C_{1-10}$ alkyl group; wherein:

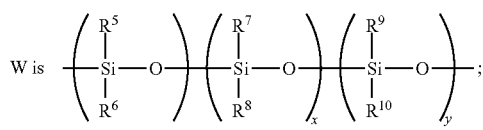

and
wherein $R^1$ and $R^4$ are independently $NH_2$, OH, COOH, SH, an epoxide, a succunic anhydride, or a succinimide group; $R^2$ and $R^3$ are independently a $C_{1-10}$ alkyl group; and $R^5$, $R^6$, $R^7$, $R^8$, $R^9$, $R^{10}$, $R^{11}$, and $R^{12}$ are independently Hydrogen, a $C_{1-10}$ alkyl group, or a $C_{1-10}$—$R^{13}$ group such that $R^{13}$ is independently a phosphate, a sulfate, a sulfonate, a betaine, a carboxylic acid, an amino acid, a diacids, a bisphosphate, or a phosphatidylcholine group, whereas multiple groups of $R^7$, $R^8$, $R^9$, $R^{10}$, $R^{11}$, $R^{12}$, and $R^{13}$ may be identical or different; wherein $NH_2$, OH, COOH, or SH is not present when the epoxide, the succunic anhydride, or the succinimide group is present; wherein at least one of $R^5$, $R^6$, $R^7$, $R^8$, $R^9$, $R^{10}$, $R^{11}$, and $R^{12}$ includes the $C_{1-10}$—$R^{13}$ group; wherein at least one of $R^7$ and $R^8$ includes the $C_{1-10}$—$R^{13}$ group; wherein $R^5$, $R^6$, $R^{11}$, and $R^{12}$ are independently a $C_{1-10}$ alkyl group; wherein:

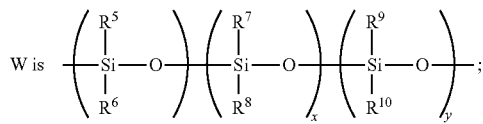

and
wherein $R^1$ and $R^4$ are independently Hydrogen, a phosphate, a sulfate, a sulfonate, a betaine, a carboxylic acid, an amino acid, a diacids, a bisphosphate, or a phosphatidylcholine group, provided at least one of $R^1$ and $R^4$ is not Hydrogen; $R^2$ and $R^3$ are independently a $C_{1-10}$ alkyl group; and $R^5$, $R^6$, $R^7$, $R^8$, $R^9$, $R^{10}$, and $R^{12}$ are independently Hydrogen, a $C_{1-10}$ alkyl group, or a $C_{1-10}$—$R^{13}$ group such that $R^{13}$ is independently $NH_2$, OH, COOH, SH, an epoxide, a succunic anhydride, or a succinimide group, whereas multiple groups of $R^7$, $R^8$, $R^9$, $R^{10}$, $R^{11}$, $R^{12}$, and $R^{13}$ may be identical or different, provided at least two of $R^5$, $R^6$, $R^7$, $R^8$, $R^9$, $R^{10}$, $R^{11}$, and $R^{12}$ includes the $C_{1-10}$—$R^{13}$ group; wherein $NH_2$, OH, COOH, or SH is not present when the epoxide, the succunic anhydride, or the succinimide group is present; wherein at least two of $R^5$, $R^6$, $R^7$, $R^8$, $R^9$, $R^{10}$, $R^{11}$, and $R^{12}$ includes the $C_{1-10}$—$R^{13}$ group; wherein x ranges from 1-50, y ranges from 25-250, and m is 1; wherein the adhesion promoter includes a first component and a second component, a) the first component is characterized by the following formula (IIa): $R^1$—$R^2$—W—Z—$R^3$—$R^4$ (IIa); wherein $R^1$ and $R^4$ are independently $NH_2$, OH, COOH, or SH; $R^2$ and $R^3$ are independently a $C_{1-10}$ alkyl group;

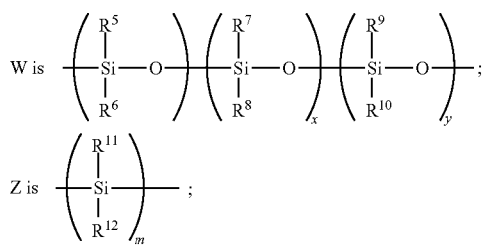

$R^5$, $R^6$, $R^7$, $R^8$, $R^9$, $R^{10}$, $R^{11}$ and $R^{12}$ are independently Hydrogen, a $C_{1-10}$ alkyl group, or a $C_{1-10}$—$R^{13}$ group such that $R^{13}$ is independently a phosphate, a sulfate, a sulfonate, a betaine, a carboxylic acid, an amino acid, a diacids, a bisphosphate, or a phosphatidylcholine group, whereas multiple groups of $R^5$, $R^6$, $R^7$, $R^8$, $R^9$, $R^{10}$, $R^{11}$, $R^{12}$, and $R^{13}$ may be identical or different; x is an integer from 1 to 1000, multiple groups of x may be identical or different; y is an integer from 1 to 1000, multiple groups of y may be identical or different; and m is an integer from 1 to 10, multiple groups of m may be identical or different; and b) the second component is characterized by the following formula (IIb): $R^{13}$—$R^{14}$—W—Z—$R^{15}$—$R^{16}$ (IIb); wherein $R^{13}$ and $R^{16}$ are independently an epoxide, a succunic anhydride, or a succinimide group; $R^{14}$ and $R^{15}$ are independently a $C_{1-10}$ alkyl group;

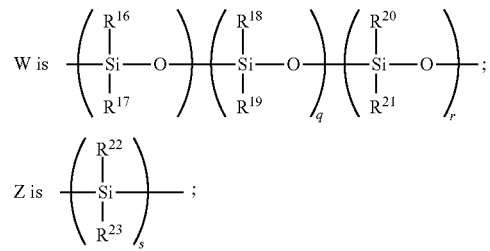

$R^{16}$, $R^{17}$, $R^{18}$, $R^{19}$, $R^{20}$, $R^{21}$, $R^{22}$, and $R^{23}$ are independently Hydrogen, a $C_{1-10}$ alkyl group, or a $C_{1-10}$—$R^{24}$ group such that $R^{24}$ is independently a phosphate, a sulfate, a sulfonate, a betaine, a carboxylic acid, an amino acid, a diacids, a bisphosphate, or a phosphatidylcholine group, whereas multiple groups of $R^{16}$, $R^{17}$, $R^{18}$, $R^{19}$, $R^{20}$, $R^{21}$, $R^{22}$, $R^{23}$, and $R^{24}$ may be identical or different; q is an integer from 1 to 1000, multiple groups of q may be identical or different; r is an integer from 1 to 1000, multiple groups of r may be identical or different; and s is an integer from 1 to 10, multiple groups of s may be identical or different; wherein i) at least one of $R^5$, $R^6$, $R^7$, $R^8$, $R^9$, $R^{10}$, $R^{11}$, $R^{12}$ includes the $C_{1-10}$—$R^{13}$ group; and/or ii) at least one of $R^{16}$, $R^{17}$, $R^{18}$, $R^{19}$, $R^{20}$, $R^{21}$, $R^{22}$, and $R^{23}$ includes the $C_{1-10}$—$R^{24}$ group; wherein i) at least one of $R^7$ and $R^8$ includes the $C_{1-10}$—$R^{13}$ group; and/or ii) at least one of $R^{18}$ and $R^{19}$ includes the $C_{1-10}$—$R^{24}$ group; wherein x ranges from 1-50, y ranges from 25-250, and m is 1 and wherein q ranges from 1-50, r ranges from 25-250, and s is 1; wherein the adhesion promoter includes a first component and a second component, a) the first component is characterized by the following formula (IIIa): $R^1$—$R^2$—W—Z—$R^3$—$R^4$ (IIIa); wherein $R^1$ and $R^4$ are independently Hydrogen, a phosphate, a sulfate, a sulfonate, a betaine, a carboxylic acid, an amino acid, a diacids, a bisphosphate, or a phosphatidylcholine group, provided at least one of $R^1$ and $R^4$ is not Hydrogen; $R^2$ and $R^3$ are independently a substituted or unsubstituted $C_{1-10}$ alkyl group;

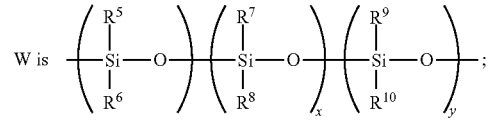

-continued

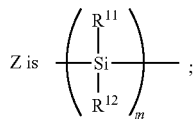

$R^5$, $R^6$, $R^7$, $R^8$, $R^9$, $R^{10}$, $R^{11}$ and $R^{12}$ are independently Hydrogen, a $C_{1-10}$ alkyl group, or a $C_{1-10}$—$R^{13}$ group such that $R^{13}$ is independently $NH_2$, OH, COOH, SH, whereas multiple groups of $R^7$, $R^8$, $R^9$, $R^{10}$, $R^{11}$, $R^{12}$, and $R^{13}$ may be identical or different; x is an integer from 1 to 1000, multiple groups of x may be identical or different; y is an integer from 1 to 1000, multiple groups of y may be identical or different; and m is an integer from 1 to 10, multiple groups of m may be identical or different; and b) the second component is characterized by the following formula (IIIb): $R^{13}$—$R^{14}$—W—Z—$R^{15}$—$R^{16}$ (IIIb); wherein $R^{13}$ and $R^{16}$ are independently Hydrogen, a phosphate, a sulfate, a sulfonate, a betaine, a carboxylic acid, an amino acid, a diacids, a bisphosphate, or a phosphatidylcholine group, provided at least one of $R^1$ and $R^4$ is not Hydrogen; $R^{14}$ and $R^{15}$ are independently a substituted or unsubstituted $C_{1-10}$ alkyl group;

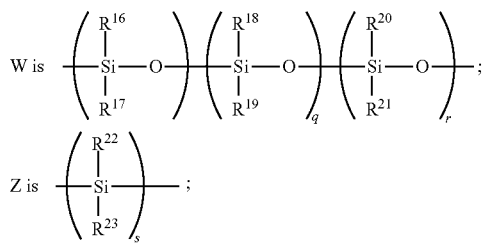

$R^{16}$, $R^{17}$, $R^{18}$, $R^{19}$, $R^{20}$, $R^{21}$, $R^{22}$, and $R^{23}$ are independently Hydrogen, a $C_{1-10}$ alkyl group, or a $C_{1-10}$—$R^{24}$ group such that $R^{24}$ is independently an epoxide, a succunic anhydride, or a succinimide group, whereas multiple groups of $R^{16}$, $R^{17}$, $R^{18}$, $R^{19}$, $R^{20}$, $R^{21}$, $R^{22}$, $R^{23}$, and $R^{24}$ may be identical or different; q is an integer from 1 to 1000, multiple groups of q may be identical or different; r is an integer from 1 to 1000, multiple groups of r may be identical or different; and s is an integer from 1 to 10, multiple groups of s may be identical or different; wherein i) at least one of $R^5$, $R^6$, $R^7$, $R^8$, $R^9$, $R^{10}$, $R^{11}$, $R^{12}$ includes the $C_{1-10}$—$R^{13}$ group; and/or ii) at least one of $R^{16}$, $R^{17}$, $R^{18}$, $R^{19}$, $R^{20}$, $R^{21}$, $R^{22}$, and $R^{23}$ includes the $C_{1-10}$—$R^{24}$ group; wherein x ranges from 1-50, y ranges from 25-250, and m is 1; and wherein q ranges from 1-50, r ranges from 25-250, and s is 1; wherein adhesion promoter is characterized by the following formula (IV): $R^1$—W—Z—$R^2$ (IV) wherein $R^1$ and $R^2$ are independently a substituted or unsubstituted $C_{1-11}$ alkyl group;

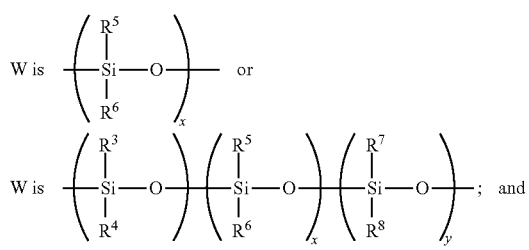

-continued

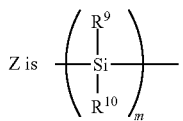

wherein $R^3$, $R^4$, $R^5$, $R^6$, $R^7$, $R^8$, $R^9$, and $R^{10}$ are independently Hydrogen, a $C_{1-10}$ alkyl group, or a $C_{1-10}$—$R^{11}$ group such that $R^{11}$ is independently $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group; whereas multiple groups of $R^3$, $R^4$, $R^5$, $R^6$, $R^7$, $R^8$, $R^9$, $R^{10}$, and $R^{11}$ may be identical or different; provided that at least one of $R^3$, $R^4$ $R^5$, $R^6$, $R^7$, and $R^8$ includes the $C_{1-10}$—$R^{11}$ group; x is an integer from 1 to 1000, multiple groups of x may be identical or different; y is an integer from 1 to 1000, multiple groups of y may be identical or different; and m is an integer from 1 to 10, multiple groups of m may be identical or different; wherein $NH_2$, OH, COOH, or SH is not present when the epoxide, the succunic anhydride, or the succinimide group is present; wherein

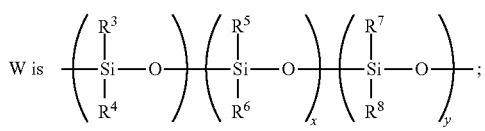

and
wherein $R^3$, $R^4$, $R^7$, $R^8$, $R^9$, $R^{10}$, and $R^{11}$ include the $C_{1-10}$ alkyl group; x ranges from 1-50; y ranges from 25-250; and m is 1; wherein the adhesion promoter includes a first component and a second component, a) the first component is characterized by the following formula (IVa): $R^1$—W—Z—$R^2$ (IVa) wherein $R^1$ and $R^2$ are independently a substituted or unsubstituted alkyl $C_{1-11}$ alkyl group;

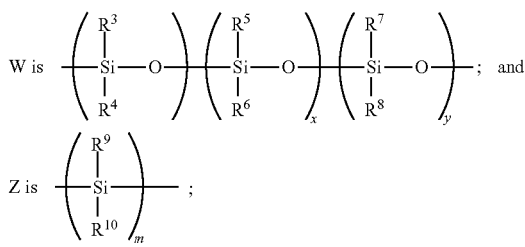

wherein $R^3$, $R^4$, $R^5$, $R^6$, $R^7$, $R^8$, $R^9$, and $R^{10}$ are independently Hydrogen, a $C_{1-10}$ alkyl group, or a $C_{1-10}$—$R^{11}$ group such that $R^{11}$ is independently $NH_2$, OH, COOH, or SH; whereas multiple groups of $R^3$, $R^4$, $R^5$, $R^6$, $R^7$, $R^8$, $R^9$, $R^{10}$, and $R^{11}$ may be identical or different; provided that at least one of $R^3$, $R^4$ $R^5$, $R^6$, $R^7$, and $R^8$ includes the $C_{1-10}$—$R^{11}$ group; x is an integer from 1 to 1000, multiple groups of x may be identical or different; y is an integer from 1 to 1000, multiple groups of y may be identical or different; and m is an integer from 1 to 10, multiple groups of m may be identical or different; and b) the second component is characterized by the following formula (IVb): $R^{12}$—W—Z—$R^{13}$ (IVb) wherein $R^{12}$ and $R^{13}$ are independently a substituted or unsubstituted $C_{1-11}$ alkyl group;

W is 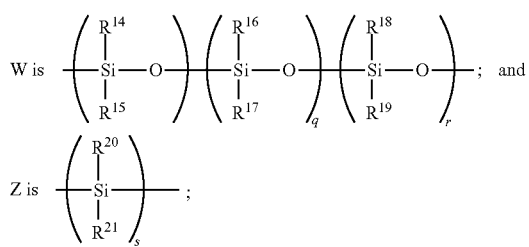 ; and

Z is $\left(\begin{array}{c} R^{20} \\ | \\ -Si- \\ | \\ R^{21} \end{array}\right)_s$ ;

wherein $R^{14}$, $R^{15}$, $R^{16}$, $R^{17}$, $R^{18}$, $R^{19}$, $R^{20}$, and $R^{21}$ are independently Hydrogen, a $C_{1-10}$ alkyl group, or a $C_{1-10}$—$R^{22}$ group such that $R^{22}$ is independently an epoxide, a succunic anhydride, or a succinimide group; whereas multiple groups of $R^{14}$, $R^{15}$, $R^{16}$, $R^{17}$, $R^{18}$, $R^{19}$, $R^{20}$, $R^{21}$, and $R^{22}$ may be identical or different; provided that at least one of $R^{14}$, $R^{15}$, $R^{16}$, $R^{17}$, $R^{18}$, and $R^{19}$ includes the $C_{1-10}$—$R^{11}$ group; q is an integer from 1 to 1000, multiple groups of x may be identical or different; r is an integer from 1 to 1000, multiple groups of y may be identical or different; and s is an integer from 1 to 10, multiple groups of m may be identical or different; wherein i) at least one of $R^5$, $R^6$, $R^7$, and $R^8$ includes the $C_{1-10}$—$R^{11}$ group; and ii) at least one of $R^{16}$, $R^{17}$, $R^{18}$, and $R^{19}$ includes the $C_{1-10}$—$R^{22}$ group; wherein x ranges from 1-50, y ranges from 25-250, and m is 1; and wherein q ranges from 1-50, r ranges from 25-250, and s is 1; wherein i) at least one of $R^5$, $R^6$, $R^7$, and $R^8$ is independently a $C_{1-10}$—$R^{23}$ group such that $R^{23}$ is a phosphate, a sulfate, a sulfonate, a betaine, a carboxylic acid, an amino acid, a diacids, a bisphosphate, or a phosphatidylcholine group; whereas multiple groups of $R^5$, $R^6$, $R^7$, and $R^8$ may be identical or different; and/or ii) at least one of $R^{16}$, $R^{17}$, $R^{18}$, and $R^{19}$ is independently a $C_{1-10}$—$R^{24}$ group such that $R^{24}$ is a phosphate, a sulfate, a sulfonate, a betaine, a carboxylic acid, an amino acid, a diacids, a bisphosphate, or a phosphatidylcholine group; whereas multiple groups of $R^{16}$, $R^{17}$, $R^{18}$, and $R^{19}$ may be identical or different; wherein the adhesion promoter is characterized by the following formula (V): $R^1$—$R^2$—W—$R^3$—$R^4$ (V) wherein $R^1$ and $R^4$ are independently Hydrogen, $NH_2$, OH, COOH, SH, an epoxide, a succunic anhydride, or a succinimide group; $R^2$ and $R^3$ are independently a $C_{1-1000}$ alkyl group; and

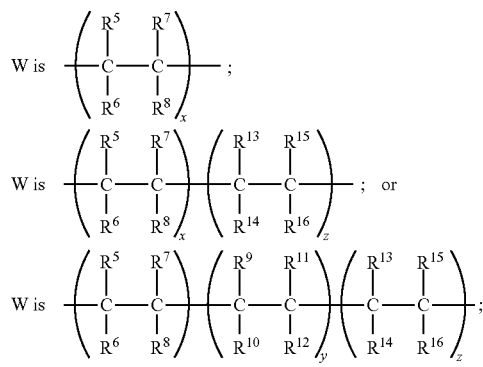

wherein $R^5$, $R^6$, $R^7$, $R^8$, $R^9$, $R^{10}$, $R^{11}$, $R^{12}$, $R^{13}$, $R^{14}$, $R^{15}$, and $R^{16}$ are independently Hydrogen, a $C_{1-10}$ alkyl group, or contain a linking group being linked to a $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, a phospha- tidylcholine, a hydrocarbon, or a silicone, the linking group being selected from the group consisting of an acrylate group, a (meth)acrylate group, a siloxy acrylate group, a vinyl group, and an allyl group, whereas at least one of $R^5$, $R^6$, $R^7$, $R^8$, $R^9$, $R^{10}$, $R^{11}$, $R^{12}$, $R^{13}$, $R^{14}$, $R^{15}$, and $R^{16}$ contains the linking group and whereas multiple groups of $R^5$, $R^6$, $R^7$, $R^8$, $R^9$, $R^{10}$, $R^{11}$, $R^{12}$, $R^{13}$, $R^{14}$, $R^{15}$, and $R^{16}$ may be identical or different; x is an integer from 1 to 1000, multiple groups of x may be identical or different; y is an integer from 1 to 1000, multiple groups of y may be identical or different; and z is an integer from 1 to 1000, multiple groups of z may be identical or different; wherein $NH_2$, OH, COOH, or SH is not present when the epoxide, the succunic anhydride, or the succinimide group is present; wherein at least one of $R^1$ and $R^2$ is $NH_2$, OH, COOH, SH, an epoxide, a succunic anhydride, or a succinimide group; wherein at least one of $R^{13}$, $R^{14}$, $R^{15}$, and $R^{16}$ contains the linking group being linked to a $NH_2$, OH, COOH, SH, an epoxide, a succunic anhydride, or a succinimide group; wherein at least one of $R^5$, $R^6$, $R^7$, $R^8$ $R^9$, $R^{10}$, $R^{11}$, and $R^{12}$ contains the linking group being linked to a phosphate, a sulfate, a sulfonate, a betaine, a carboxylic acid, an amino acid, a diacids, a bisphosphate, a phosphatidylcholine, a hydrocarbon, or a silicone; wherein the silicone includes a Tris(trimethylsiloxy)silyl group; wherein W is 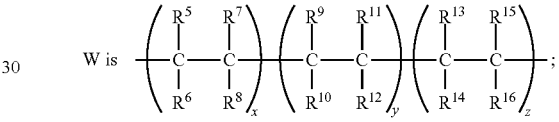 ;

wherein $R^5$, $R^6$, $R^7$, and $R^8$ are independently a $C_{1-10}$ alkyl group or contain a linking group being linked to a phosphate, a sulfate, a sulfonate, a betaine, a carboxylic acid, an amino acid, a diacids, a bisphosphate, or a phosphatidylcholine, the linking group being selected from the group consisting of an acrylate group, a (meth)acrylate group, a siloxy acrylate group, a vinyl group, and an allyl group, whereas at least one of $R^5$, $R^6$, $R^7$, and $R^8$ contains the linking group and whereas multiple groups of $R^5$, $R^6$, $R^7$, and $R^8$ may be identical or different; $R^9$, $R^{10}$, $R^{11}$, and $R^{12}$ are independently a $C_{1-10}$ alkyl group or contain a linking group being linked to a hydrocarbon or a silicone, the linking group being selected from the group consisting of an acrylate group, a (meth)acrylate group, a siloxy acrylate group, a vinyl group, and an allyl group, whereas at least one of $R^9$, $R^{10}$, $R^{11}$, and $R^{12}$ contains the linking group and whereas multiple groups of $R^9$, $R^{10}$, $R^{11}$, and $R^{12}$ may be identical or different; $R^{13}$, $R^{14}$, $R^{15}$, and $R^{16}$ are independently a $C_{1-10}$ alkyl group or contain a linking group being linked to a $NH_2$, OH, COOH, SH, an epoxide, a succunic anhydride, or a succinimide group, the linking group being selected from the group consisting of an acrylate group, a (meth)acrylate group, a siloxy acrylate group, a vinyl group, and an allyl group, whereas at least one of $R^{13}$, $R^{14}$, $R^{15}$, and $R^{16}$ contains the linking group and whereas multiple groups of $R^{13}$, $R^{14}$, $R^{15}$, and $R^{16}$ may be identical or different; x is an integer from 1 to 100, multiple groups of x may be identical or different; y is an integer from 1 to 100, multiple groups of y may be identical or different; and z is an integer from 1 to 100, multiple groups of z may be identical or different; wherein $NH_2$, OH, COOH, or SH is not present when the epoxide, the succunic anhydride, or the succinimide group is present; wherein the silicone includes a Tris(trimethylsiloxy)silyl group; wherein the adhesion promoter includes a first component and a second component, a) the first component is characterized by the following formula (VIa): $R^1$—$R^2$—W—$R^3$—$R^4$ (VIa); wherein $R^1$ and $R^4$ are independently Hydrogen, an epoxide, a succunic anhydride, or a succinimide group; $R^2$ and $R^3$ are independently a $C_{1\text{-}1000}$ alkyl group; and

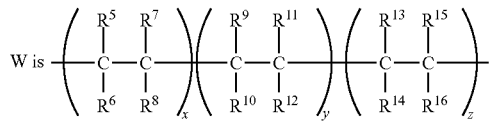

wherein $R^5$, $R^6$, $R^7$, and $R^8$ are independently Hydrogen, a $C_{1\text{-}10}$ alkyl group, or contain a linking group being linked to a phosphate, a sulfate, a sulfonate, a betaine, a carboxylic acid, an amino acid, a diacids, a bisphosphate, a phosphatidylcholine, a hydrocarbon, or a silicone, the linking group being selected from the group consisting of an acrylate group, a (meth)acrylate group, a siloxy acrylate group, a vinyl group, and an allyl group, whereas at least one of $R^5$, $R^6$, $R^7$, and $R^8$ contains the linking group and whereas multiple groups of $R^5$, $R^6$, $R^7$, and $R^8$ may be identical or different; $R^9$, $R^{10}$, $R^{11}$, and $R^{12}$ are independently Hydrogen, a $C_{1\text{-}10}$ alkyl group, or contain a linking group being linked to a hydrocarbon or a silicone group, the linking group being selected from the group consisting of an acrylate group, a (meth)acrylate group, a siloxy acrylate group, a vinyl group, and an allyl group, whereas at least one of $R^9$, $R^{10}$, $R^{11}$, and $R^{12}$ contains the linking group and whereas multiple groups of $R^9$, $R^{10}$, $R^{11}$, and $R^{12}$ may be identical or different; $R^{13}$, $R^{14}$, $R^{15}$, and $R^{16}$ are independently Hydrogen, a $C_{1\text{-}10}$ alkyl group, or contain a linking group being linked to an epoxide, a succunic anhydride, or a succinimide group, the linking group being selected from the group consisting of an acrylate group, a (meth)acrylate group, a siloxy acrylate group, a vinyl group, and an allyl group, whereas at least one of $R^{13}$, $R^{14}$, $R^{15}$, and $R^{16}$ contains the linking group and whereas multiple groups of $R^{13}$, $R^{14}$, $R^{15}$, and $R^{16}$ may be identical or different; x is an integer from 1 to 1000, multiple groups x may be identical or different; and y is an integer from 1 to 1000, multiple groups y may be identical or different; and z is an integer from 1 to 1000, multiple groups z may be identical or different; and b) the second component is characterized by the following formula (VIb): $R^{17}$—$R^{18}$—W—$R^{19}$—$R^{20}$ (VIb); wherein $R^{17}$ and $R^{20}$ are independently Hydrogen, $NH_2$, OH, COOH, or SH; $R^{18}$ and $R^{19}$ are independently a $C_{1\text{-}1000}$ alkyl group; and

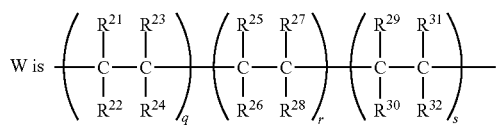

wherein $R^{21}$, $R^{22}$, $R^{23}$, and $R^{24}$ are independently Hydrogen, a $C_{1\text{-}10}$ alkyl group, or contain a linking group being linked to a phosphate, a sulfate, a sulfonate, a betaine, a carboxylic acid, an amino acid, a diacids, a bisphosphate, a phosphatidylcholine, a hydrocarbon, or a silicone, the linking group being selected from the group consisting of an acrylate group, a (meth)acrylate group, a siloxy acrylate group, a vinyl group, and an allyl group, whereas at least one of $R^{21}$, $R^{22}$, $R^{23}$, and $R^{24}$ contains the linking group and whereas multiple groups of $R^{21}$, $R^{22}$, $R^{23}$, and $R^{24}$ may be identical or different; $R^{25}$, $R^{26}$, $R^{27}$, and $R^{28}$ are independently Hydrogen, a $C_{1\text{-}10}$ alkyl group, or contain a linking group being linked to a hydrocarbon or a silicone group, the linking group being selected from the group consisting of an acrylate group, a (meth)acrylate group, a siloxy acrylate group, a vinyl group, and an allyl group, whereas at least one of $R^{25}$, $R^{26}$, $R^{27}$, and $R^{28}$ contains the linking group and whereas multiple groups of $R^{25}$, $R^{26}$, $R^{27}$, and $R^{28}$ may be identical or different; $R^{29}$, $R^{30}$, $R^{31}$, and $R^{32}$ are independently Hydrogen, a $C_{1\text{-}10}$ alkyl group, or contain a linking group being linked to a $NH_2$, OH, COOH, or SH group, the linking group being selected from the group consisting of an acrylate group, a (meth)acrylate group, a siloxy acrylate group, a vinyl group, and an allyl group, whereas at least one of $R^{29}$, $R^{30}$, $R^{31}$, and $R^{32}$ contains the linking group and whereas multiple groups of $R^{29}$, $R^{30}$, $R^{31}$, and $R^{32}$ may be identical or different; q is an integer from 1 to 1000, multiple groups of q may be identical or different; and r is an integer from 1 to 1000, multiple groups of r may be identical or different; and s is an integer from 1 to 1000, multiple groups of s may be identical or different; wherein the silicone of the first component, the second component, or both includes a Tris(trimethylsiloxy)silyl group; wherein the Tris(trimethylsiloxy)silyl group is [tris(trimethylsilyloxy)silyl]propyl methacrylate; wherein the amine-based polymerizable compound is an amine modified polysiloxane compound; wherein the first component mixture, the second component mixture, or both include an adhesion promoter; wherein the adhesion promoter includes a silicon functionality; wherein the adhesion promoter includes a silicon functionality and an amine or epoxy functionality; wherein the first component mixture includes an adhesion promoter having a silicone functionality and an epoxy functionality; wherein the second component mixture includes an adhesion promoter having a silicone functionality and an amine functionality; wherein the first component mixture includes an adhesion promoter having a silicone functionality, an epoxy functionality, and a dentin binding functionality; wherein the second component mixture includes an adhesion promoter having a silicone functionality, an amine functionality, and a dentin binding functionality; wherein the dentin binding functionality is selected from the group consisting of a phosphate, a sulfate, a sulfonate, a betaine, a carboxylic acid, an amino acid, a diacids, a bisphosphate, and a phosphatidylcholine; wherein the composite sealant material has a viscosity over 100,000 cps or putty-like; further comprising the step of inserting a gutta-percha point, an obturator, or a cross-linked gutta-percha-point into the root canal; wherein the gutta-percha point or carrier is surface modified; wherein the surface modification is corona treatment or plasma treatment; wherein the cross-linked cis-polyisoprene microparticles are not soluble in the composite sealant material; use of the endodontic composite sealant composition described herein; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

DETAILED DESCRIPTION OF THE INVENTION

Desirably, the composite sealant composition includes a cross-linkable material, though not required.

In general, the present invention is directed to an improved high strength composite sealant composition and processes of forming the composition. Advantageously, the composite sealant composition can be employed to form dental sealants with desirable high strength characteristics. This high strength material enables the preparation of root canals and may be useful for improved bonding (higher adhesion) to the tooth dentin and/or root canal points. Dental materials containing polymerizable resins and filler particles often are used to prepare the root canals. Such dental materials can be self (chemically)-curable, heat-curable, light-curable, or dual-curable. The dental materials are cured and hardened by different chemical mechanisms to form strong and durable materials for various dental applications.

In one aspect, the invention solves the problem of the creation of a seal between the sealer and the gutta-percha AND a seal between the sealer and the dentin to prevent leakage of bacteria into the root canal. The invention uses rubber formulations cryogenically ground into a powder and mixed as a filler in various two part polymer systems. The ground rubber can be blended in either one or both parts of the polymer system. One or more types of ground rubber can be used. This will create a fluid(s) with a paste like viscosity.

The technology to make this work may not be the grinding or the dispersion into the polymer system. It is believed that the formulation of the ground rubber in relation to the polymer system provides the one of the advantages of this invention.

In another aspect the invention solves the problem of the creation of a seal between the obturation material and the dentine to prevent leakage of bacteria into the root canal. The invention is two ideal molecular additives which have been designed to bond to collagen AND hydroxyapatite.

Dentin is composed of a collagen (hydrocarbon polymer) matrix holding together crystalline hydroxyapatite (CaP). The dentin binding molecules are designed to include three subcomponents in a tri block construction. For example, in a first portion, Block A, may be composed of phosphate group, in a second portion, Block B, may be composed of tris methacrylate and in a third portion, Block C, may be either a reactive group such as an amino methacrylate or a glycidal methacrylate. Block A is designed to bond to the hydroxyapatite. Block B is designed to be a compatibilizer. Block C is designed to cross link into the network during setting (amino/epoxy reaction). The molecular additives are dispersed into two dimethylsiloxanes; an amino functionalized and an epoxy functionalized (see the attached document for more detail).

Polymerizable Materials

The polymerizable material (e.g., a composite sealant composition) typically includes at least one polymerizable component and optionally without limitation, one or more of at least one filler (e.g., glass particles), an adhesion promoter, an initiator, a catalyst, an accelerator, an inhibitor, surfactant, additive, or combinations thereof or others.

Polymerizable Compounds

Turning now in greater detail to the individual components of the overall composition. The composite sealant composition herein may include at least one polymerizable material. Desirably, the composite sealant composition may include a first polymerizable material having at least one of a cyclic compound that is capable of undergoing a ring opening reaction (e.g., a succunic anhydride, a succinimide group, an epoxide, or otherwise) a ring opening nucleophile (e.g., OH, COOH, SH, an amine resin (e.g., $NH_2$), or otherwise), urethane di-(meth)acrylate, multi(meth)acrylate derivatives of isocyanatomethyl cyclohexane, a polymerizable polysiloxane compound (e.g., an epoxy functionalized siloxane, an amino functionalized siloxane, or otherwise), or any combination thereof.

The first polymerizable material may typically be present in an amount of at least about 1%, preferably at least about 5%, and more preferable at least about 10% by wt the composite sealant composition. Furthermore, it is appreciated that the first polymerizable material may typically be present in an amount of less than about 99%, preferably less than about 75% and preferably less than about 50% by wt the overall composite sealant composition. For example, the first polymerizable material may typically be present in an amount ranging from about 1% to about 99%, preferably from about 5% to about 75%, and more preferably from about 10% to about 50% by wt the overall composite sealant composition. In one specific embodiment, the first polymerizable material is the polymerizable polysiloxane compound.

Examples of polymerizable polysiloxane compounds (e.g., polydimethylsiloxane copolymers) that may be used in the composition of this invention, include, but are not limited to, cyclic compounds that are capable of undergoing a ring opening reaction such as epoxy modified polysiloxane compounds (e.g., difunctional and multifunctional epoxy silicones) and ring opening nucleophiles such as amine modified polysiloxane compounds (e.g., aminoalkyl functional silicones). One preferred epoxy modified polysiloxane is sold under the Tradename EMS 622 and is commercially available from Gelest, Inc. One preferred amine modified polysiloxane is sold under the Tradename AMS 162 and is commercially available from Gelest, Inc.

The first polymerizable material may include a first component (e.g., a cyclic compound that is capable of undergoing a ring opening reaction) and a second component (e.g., ring opening nucleophile) capable of polymerization. For example, the polysiloxane compound may include a first polysiloxane component having an epoxy modified polysiloxane or a second polysiloxane component having an amine modified polysiloxane. The epoxy modified polysiloxane may be present in an amount of at least about 1%, preferably at least about 3%, and more preferable at least about 5% by wt the overall composite sealant composition. Furthermore, the epoxy modified polysiloxane may be present in an amount of less than about 50%, preferably less than about 40% and preferably less than about 25% by wt the overall composite sealant composition. For example, the epoxy modified polysiloxane may be present in an amount ranging from about 1% to about 50%, preferably from about 3% to about 40%, and more preferably from about 5% to about 25% by wt the overall composite sealant composition. An example of the first polysiloxane component having the epoxy modified polysiloxane may be present as formula (I).

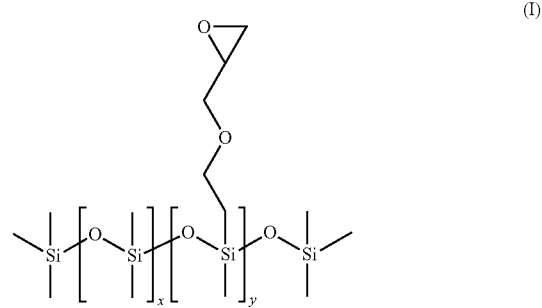

(I)

wherein x is 1-1000, and y is 1-1000.

Alternatively or in addition to the first polysiloxane component having an epoxy modified polysiloxane, the polysiloxane component may include a second polysiloxane component having an amine modified polysiloxane. The amine modified polysiloxane may be present in an amount of at least about 1%, preferably at least about 3%, and more preferable at least about 5% by wt the overall composite sealant composition. Furthermore, the amine modified polysiloxane may be present in an amount of less than about 50%, preferably less than about 40% and preferably less than about 25% by wt the overall composite sealant composition. For example, the amine modified polysiloxane may be present in an amount ranging from about 1% to about 50%, preferably from about 3% to about 40%, and more preferably from about 5% to about 25% by wt the overall composite sealant composition.

One preferred initiating component includes an alkanol amine. Examples of suitable alkanol amines include, but are not limited to ethanolamine, 2-amino-1-butanol, 4-amino-1-butanol, 2-aminoethanthiol, 2-amino-1-hexanol, 2-amino-3-methyl-1-butanol, 2-amino-2-methyl-1-propanol, 2-amino-2-methyl-1,3-propanediol, 5-amino-1-pentanol, 2-(methylamino) ethanol, 2-(propylamino)ethanol, tris(hydroxymethyl)aminomethane, 2-amino-1-propanol, 2-amino-1-pentanol, ethanolamine, 2-hydroxyethylhydoradine, 3-amino-1-propanol, DL-2-amino-1-propanol, DL-1-amino-2-propanol, DL-2-amino-1-pentanol, DL-2-Amino-1-hexanol, 6-amino-1-hexanol, 2-(2-aminoethoxy) ethanol, or otherwise and combinations thereof. Other catalysts are appreciated such as salts (e.g., platinum, palladium, or otherwise).

As shown in Table 1, an example of acceleration effects for curing various composite sealant compositions of the two-component systems with different catalysts:

TABLE 1

| I.D. | 712A11 | 712B11 | 712C11 | 712D11 | 712 E11 | 712U11 |
|---|---|---|---|---|---|---|
| AMS 162 | 50.3% | 49.5% | 49.3% | 49.4% | 49.0% | 85.8% |
| EMS 622 | 49.7% | 49.5% | 49.7% | 49.5% | 50.0% | 14.2% |
| 2-amino-3methyl-butanol | 0.0% | 1.0% | 0.0% | 0.0% | 0.0% | 0.0% |
| dl-2-amino-1-pentanol | 0.0% | 0.0% | 1.0% | 0.0% | 0.0% | 0.0% |
| dl-2-amino-1-hexanol | 0.0% | 0.0% | 0.0% | 1.0% | 0.0% | 0.0% |
| 6-amino-1-hexanol | 0.0% | 0.0% | 0.0% | 0.0% | 1.0% | 0.0% |
| Total Mass (g) | 10.1 | 10.1 | 10.1 | 10.1 | 10.3 | 10.0 |
| Time after mixing to full cure (days) | 5 | 3 | 3 | 3 | 5 | Not Set, >15 |

An example of the second polysiloxane component having the amine modified polysiloxane may be present as formula (II).

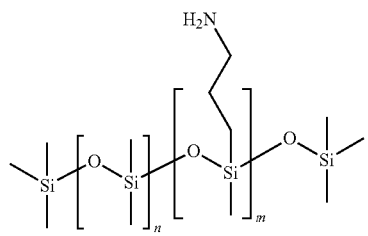

(II)

wherein n is 1-1000, and m is 1-1000.

Curing Agent

The composite sealant composition herein may include at least one initiating component (e.g., catalyst) to effectuate curing of the material. The initiating component may be present in an amount of at least about 0.0005%, preferably at least about 0.005%, and more preferably at least about 0.05% by wt the overall composite sealant composition. The overall composite sealant composition may include less than about 3.0%, preferably less than about 1.5%, and more preferably less than about 1% wt of the initiating component. For example, the initiating component may be present in a range of about 0.0005% to about 3%, preferably from about 0.005% to about 1.5%, and more preferably from about 0.05% to about 1% wt of the overall composite sealant composition.

Filler

The composite sealant compositions may include one or more fillers. Fillers having radiopacity useful in accordance with the invention, without limitation, include inorganic fillers such as Ag, $TiO_2$, $La_2O_3$, $ZrO_2$, $BaSO_4$, $CaWO_4$, $BaWO_4$, $Fe_2O_3$ and $Bi_2O_3$, $CeO_2$, $ZrO_2$, MgO, lanthanide salts, polymer granulates, barium or strontium-containing glass. The glass may contain fluoride for fluoride release in vivo. When included, the radiopacifier may be present in an amount of at least about 20%, preferably at least about 30%, and more preferable at least about 40% by wt the overall composite sealant composition. Furthermore, the radiopacifier may be present in an amount of less than about 80%, preferably less than about 70% and preferably less than about 60% by wt the overall composite sealant composition. For example, the radiopacifier may be present in an amount ranging from about 20% to about 80%, preferably from about 30% to about 70%, and more preferably from about 40% to about 60% by wt the overall composite sealant composition.

Other fillers that may be employed include, but are not limited to silicas, aluminas, magnesias, titanias, inorganic salts, metallic oxides, (e.g., zinc oxides, calcium hydroxide, or otherwise) and glasses. In one desired embodiment, precipitated silica (e.g., Hi-Sil 233) may be included as a filler. In another desired embodiment, fumed silica (e.g., Aerosil 200) may be included as a filler. The filler material may be present in an amount of at least about 0.1%, preferably at least about 1%, and more preferably at least about 5% by wt the overall composite sealant composition. Furthermore, the filler material may be present in an amount of less than about 25%, preferably less than about 20% and more preferably less than about 15% by wt the overall composite sealant composition. For example, the filler material may be present in an amount ranging from about 0.1% to about 25%, preferably from about 1% to about 20%, and more preferably from about 5% to about 15% by wt the overall composite sealant composition.

In a preferred embodiment, the composite sealant composition may further include a cross-linked material (e.g., cross-linked rubber such as polyisoprene or otherwise). A desirable example of a cross-linked material may include a cross-linked cis-polyisoprene-based material such as a cis-1,4-polyisoprene-based material. As shown in Tables 2 and 3, the cross-linked material may include the following compositions as described in U.S. Ser. No. 13/045,744, filed Mar. 11, 2011, which is herein incorporated by reference for all purposes:

TABLE 2

| Component | Weight % |
|---|---|
| 1-4, Polyisoprene | 10 to 40 |
| Curing Agent | 0.1 to 30 |
| Curing Co agent | 0.01 to 30 |
| Zinc Oxide | 0 to 80 |
| Radiopacifier | 0 to 40 |
| Reinforcing Fillers | 0 to 50 |
| Carbon Nanotubes | 0 to 50 |
| Fibers | 0 to 50 |
| Colorant | 0 to 10 |

TABLE 3

| Component | Weight % |
|---|---|
| Cross-Linkable Material | 10 to 40 |
| Rubber | 0.5 to 15 |
| Curing Agent | 0.1 to 30 |
| Curing Co agent | 0.01 to 15 |
| Antimicrobial | 0.01 to 50 |
| Radiopacifier | 5.0 to 60 |
| Reinforcing Fillers | 0.5 to 30 |
| Fibers | 0.5 to 30 |
| Colorant | 0.01 to 25 |
| Anti Oxidant | 0 to 10 |
| Processing Aid | 0 to 10 |

The cross-linked material may be present in an amount of at least about 3%, preferably at least about 5%, and more preferably at least about 10% by wt the overall composite sealant composition. Furthermore, the cross-linked material may be present in an amount of less than about 50%, preferably less than about 40% and more preferably less than about 30% by wt the overall composite sealant composition. For example, the cross-linked material may be present in an amount ranging from about 3% to about 50%, preferably from about 5% to about 40%, and more preferably from about 10% to about 30% by wt the overall composite sealant composition.

Desirably, the cross-linked material may be provided as a powder (e.g., from a grinding or chopping process of the cross-linked material). The cross-linked material may include a particle size of at least about 5, preferably at least about 10 and more preferably at least about 25 microns. Furthermore, the cross-linked material may include a particle size of less than about 500, preferably less than about 400, and more preferably less than about 300 microns. For example, the cross-linked material may include a particle size ranging from about 5 to about 500, preferably from about 10 to about 300, and more preferably from about 25 to about 150 microns (e.g., from about 50 microns to about 100 microns or from about 125 microns to about 200 microns).

As shown in Table 4, one specific example of the two component composite sealant composition containing a cross-linked material:

TABLE 4

| Component A | Weight % | Component B | Weight % |
|---|---|---|---|
| Reactive-cyclic-based Polymerizable Compound | 5.0 to 50 | Ring-opening-based Polymerizable Compound | 5.0 to 50 |
| Catalyst | 0 | Catalyst | 0.001 to 5.0 |
| Radiopacifier | 20 to 80 | Radiopacifier | 20 to 80 |
| Reinforcing Fillers | 0.1 to 25 | Reinforcing Fillers | 0.1 to 25 |
| Cross-linked Rubber | 0.1 to 50 | Cross-linked Rubber | 0.1 to 50 |

Desirably, the cyclic-based polymerizable compound includes epoxy functionality, while the ring-opening-based polymerizable compound includes amine functionality, though not required.

The composite sealant composition may further include additives, pharmaceutical active ingredients, dyes or pigments (e.g., iron oxides) waxes, oils (e.g., silicone oil and paraffin oil), surfactants, fatty acids (e.g., stearic acid), anti-oxidants, preservatives (e.g., nanosilver), or mixtures thereof.

Adhesion Promoter

The composite sealant composition may further include at least one adhesion promoter. In one aspect, the adhesion promoter (e.g., second polymerizable material) may be present in addition to the polymerizable compound (e.g., second polymerizable material). In another aspect the adhesion promoter may be the polymerizable compound.

Without intending to be bound by theory, it is believed that the adhesion promoter herein makes advantageous employment of a particular molecular structure by which at least a portion of the molecule may include cyclic compounds that are capable of undergoing a ring opening reaction functionality (e.g., epoxy group, a succunic anhydride group, a succinimide group, or otherwise) and/or ring opening nucleophile functionality (e.g., OH, COOH, SH amine group, such as diepoxide or diamine group, or otherwise), which is capable of cross-linking the composite sealant composition. The adhesion promoter molecular structure may include hydrophobic functionality such as a hydrocarbon, a silicone (e.g., it is silanated such as SiO, $SiO_2$, $SiH_4$, or SiC), or otherwise, which is capable of being a thickener and/or may be provided as a dispersion carrier for the cross-linked material discussed herein. In one specific embodiment, the silicone functionality includes a Tris (trimethylsiloxy)silyl group such as [tris(trimethylsilyloxy)silyl]propyl methacrylate). Furthermore, the adhesion promoter molecular structure may include a dentin binding functionality, such as an phosphate, sulfate, sulfonate, betaine, carboxylic acids, amino acid, diacids, bisphosphate, or phosphatidylcholine functionality, which is capable of improving the linkage with the tooth dentin such as through the molecular network of the composite sealant composition.

The adhesion promoter may be a one component material or a two component material. Examples of the adhesion promoter include but are not limited to:

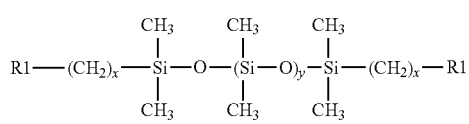

i)

wherein $R^1$ is independently $NH_2$, OH, COOH, SH, an epoxide, a succunic anhydride, or a succinimide group, whereas $R^1$ may be identical or different, (preferably $R^1$ is a ring opening nucleophile such as $NH_2$, OH, COOH, SH or otherwise);

x is an integer from 0 to 10 (e.g., 1 to 10), multiple groups of x may be identical or different; and y is an integer from 1 to 1000, multiple groups of y may be identical or different.

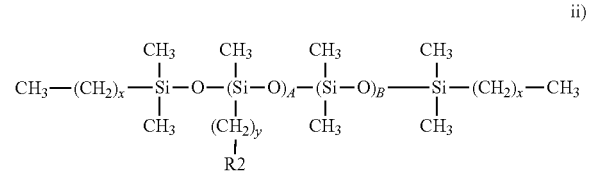

ii)

wherein $R^2$ is independently $NH_2$, OH, COOH, SH, an epoxide, a succunic anhydride, or a succinimide group, whereas multiple groups of $R^2$ may be identical or different, (preferably $R^2$ is a ring opening nucleophile such as $NH_2$, OH, COOH, SH or otherwise);

x is an integer from 0 to 10 (e.g., 1 to 10), multiple groups of x may be identical or different;

y is an integer from 1 to 10, multiple groups of y may be identical or different;

A is an integer from 1 to 1000 (e.g., 1 to 100, preferably 1 to 10), multiple groups of A may be identical or different; and B is an integer from 0 to 1000 (e.g., 1 to 100, preferably 45 to 65), multiple groups of B may be identical or different.

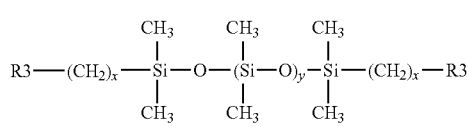

iii)

wherein $R^3$ is independently $NH_2$, OH, COOH, SH, an epoxide, a succunic anhydride, or a succinimide group, whereas $R^3$ may be identical or different, (preferably $R^3$ is a cyclic compound that may undergo ring polymerization such as an epoxide, a succunic anhydride, a succinimide group, or otherwise);

x is an integer from 0 to 10 (e.g., 1 to 10), multiple groups of x may be identical or different; and y is an integer from 1 to 1000, multiple groups of y may be identical or different.

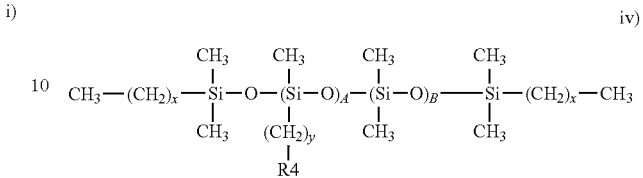

iv)

wherein $R^4$ is independently $NH_2$, OH, COOH, SH, an epoxide, a succunic anhydride, or a succinimide group, whereas multiple groups of $R^4$ may be identical or different, (preferably $R^4$ is a cyclic compound that may undergo ring polymerization such as an epoxide, a succunic anhydride, a succinimide group, or otherwise);

x is an integer from 0 to 10 (e.g., 1 to 10), multiple groups of x may be identical or different;

y is an integer from 1 to 10, multiple groups of y may be identical or different;

A is an integer from 1 to 1000, multiple groups of A may be identical or different; and B is an integer from 0 to 1000 (e.g., 1 to 1000), multiple groups of B may be identical or different.

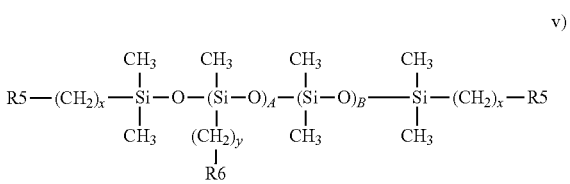

v)

wherein $R^5$ is independently $NH_2$, OH, COOH, SH, an epoxide, a succunic anhydride, or a succinimide group, whereas multiple groups of $R^5$ may be identical or different;

$R^6$ is independently a phosphate, a sulfate, a sulfonate, a betaine, a carboxylic acid, an amino acid, a diacids, a bisphosphate, or a phosphatidylcholine group, whereas multiple groups of $R^6$ may be identical or different;

x is an integer from 0 to 10 (e.g., 1 to 10), multiple groups of x may be identical or different;

y is an integer from 1 to 10, multiple groups of y may be identical or different;

A is an integer from 1 to 1000, multiple groups of A may be identical or different; and B is an integer from 0 to 1000 (e.g., 1 to 1000), multiple groups of B may be identical or different; and wherein $R^5$ and $R^6$ can change positions.

The adhesion promoter may be a one component material or a two component material. Examples of the adhesion promoter include but are not limited to:

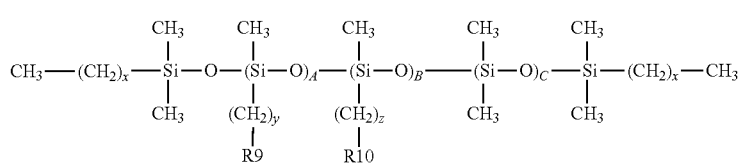

vi)

wherein $R^9$ is independently $NH_2$, OH, COOH, SH, an epoxide, a succunic anhydride, or a succinimide group, whereas multiple groups of $R^9$ may be identical or different;

$R^{10}$ is independently a phosphate, a sulfate, a sulfonate, a betaine, a carboxylic acid, an amino acid, a diacids, a bisphosphate, or a phosphatidylcholine group, whereas multiple groups of $R^{10}$ may be identical or different;

x is an integer from 0 to 10 (e.g., 1 to 10), multiple groups of x may be identical or different;

y is an integer from 1 to 10, multiple groups of y may be identical or different;

z is an integer from 1 to 10, multiple groups of z may be identical or different;

A is an integer from 1 to 1000, multiple groups of A may be identical or different; and B is an integer from 1 to 1000, multiple groups of B may be identical or different; and C is an integer from 0 to 1000 (e.g., 1 to 1000), multiple groups of C may be identical or different; and wherein $R^9$ and $R^{10}$ can change positions.

In a desired embodiment, each functional portion is present thereby forming a ter-polymer adhesion promoter.

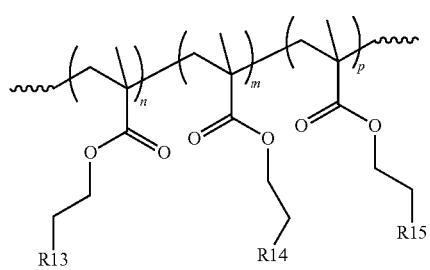

vii)

wherein $R^{13}$ is independently a phosphate, a sulfate, a sulfonate, a betaine, a carboxylic acid, an amino acid, a diacids, a bisphosphate, or a phosphatidylcholine group, whereas multiple groups of $R^{13}$ may be identical or different;

$R^{14}$ is independently a hydrophobic group such as a hydrocarbon, a silicone (e.g., it is silanated), or otherwise, (preferably the silicone includes a Tris(trimethylsiloxy)silyl group such as [tris(trimethylsilyloxy)silyl]propyl methacrylate), whereas multiple groups of $R^{14}$ may be identical or different;

$R^{15}$ is independently $NH_2$, OH, COOH, SH, an epoxide, a succunic anhydride, or a succinimide group, whereas multiple groups of $R^{15}$ may be identical or different;

n is an integer from 1 to 1000, multiple groups of x may be identical or different;

m is an integer from 0 to 1000 (e.g., 1 to 1000), multiple groups of y may be identical or different;

p is an integer from 1 to 1000, multiple groups of z may be identical or different; and wherein $R^{13}$, $R^{14}$, and $R^{15}$ can change positions.

It is appreciated that a two component adhesion promoter may include a first component of the formula i)-vii) having a cyclic compound that may undergo ring polymerization such as an epoxide, a succunic anhydride, a succinimide group, or otherwise and a second component of the formula i)-vii) having a ring opening nucleophile such as $NH_2$, OH, COOH, SH or otherwise. When included, polymerization may occur by mixing the first and second components to form the adhesion promoter.

The adhesion promoter may be synthesized by various processes. Desirably, the ter-polymer adhesion promoter may be formed by Reversible Addition-Fragmentation Chain Transfer (RAFT) polymerization to form a two component system. For example, the first component (having a cyclic compound that may undergo ring polymerization) may be formed by the following RAFT polymerization:

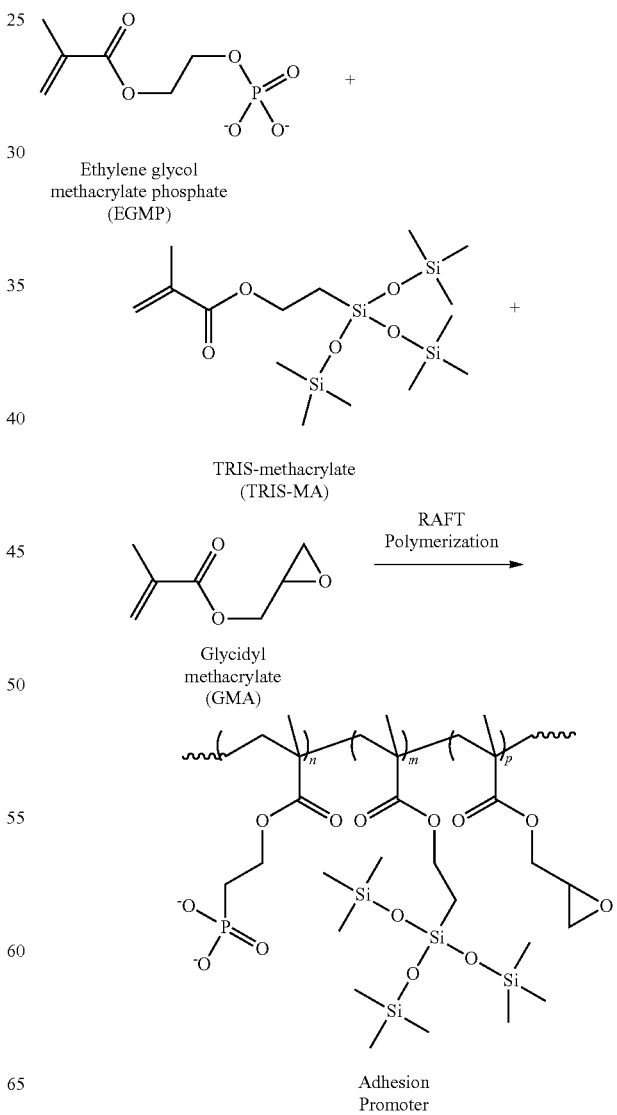

The second component (having a ring opening nucleophile) may be formed by the following RAFT polymerization:

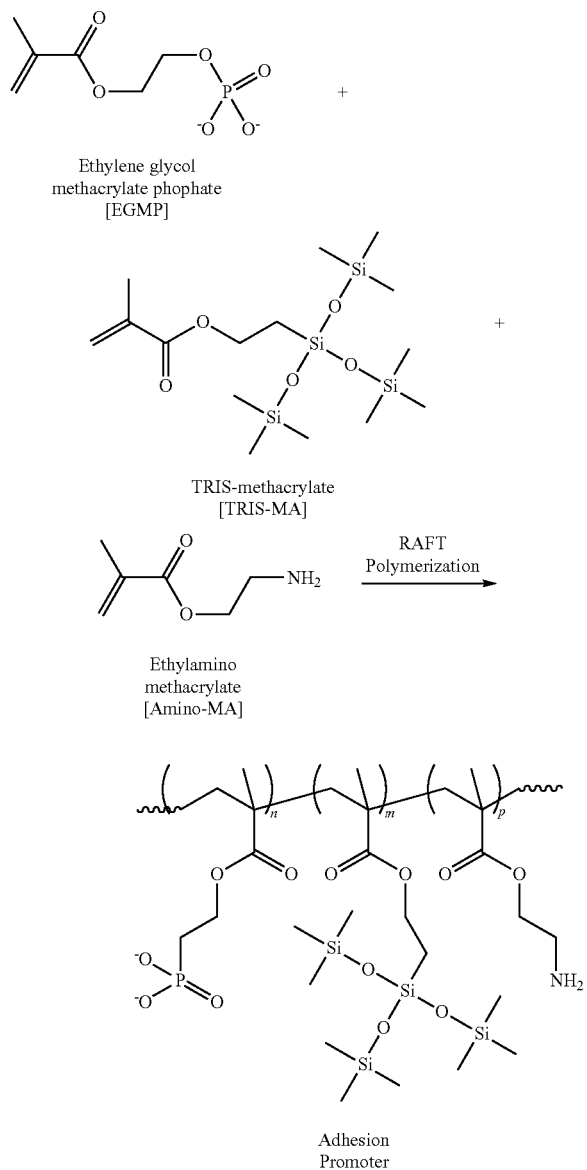

Ethylene glycol methacrylate phophate [EGMP]

TRIS-methacrylate [TRIS-MA]

Ethylamino methacrylate [Amino-MA]

Adhesion Promoter

These specific examples i)-vii) of possible adhesion promoters should not be construed as limiting examples.

In a composite sealant composition that includes at least one polymerizable compound and at least one adhesion promoter (Examples from Tables 4-7), the adhesion promoter may be present in an amount of at least about 3%, preferably at least about 5%, and more preferably at least about 10% by wt the overall composite sealant composition. Furthermore, the adhesion promoter may be present in an amount of less than about 50%, preferably less than about 40% and more preferably less than about 30% by wt the overall composite sealant composition. For example, the adhesion promoter may be present in an amount ranging from about 3% to about 50%, preferably from about 5% to about 40%, and more preferably from about 10% to about 30% by wt the overall composite sealant composition.

TABLE 4

| Component A | Weight % | Component B | Weight % |
|---|---|---|---|
| Reactive-Cyclic-based Polymerizable Compound | 5.0 to 25 | Ring-opening-based Polymerizable Compound | 5.0 to 25 |
| Catalyst | 0 | Catalyst | 0.001 to 5.0 |
| Radiopacifier | 20 to 80 | Radiopacifier | 20 to 80 |
| Reinforcing Fillers | 0.1 to 25 | Reinforcing Fillers | 0.1 to 25 |
| Cross-linked Rubber | 0.1 to 50 | Cross-linked Rubber | 0.1 to 50 |
| Reactive-Cyclic-based Adhesion Promoter | 5.0 to 25 | Ring-opening-based Adhesion Promoter | 5.0 to 25 |

TABLE 5

| Component A | Weight % | Component B | Weight % |
|---|---|---|---|
| Reactive-Cyclic-based Polymerizable Compound | 5.0 to 50 | Ring-opening-based Polymerizable Compound | 0 |
| Catalyst | 0 | Catalyst | 0.001 to 5.0 |
| Radiopacifier | 20 to 80 | Radiopacifier | 20 to 80 |
| Reinforcing Fillers | 0.1 to 25 | Reinforcing Fillers | 0.1 to 25 |
| Cross-linked Rubber | 0.1 to 50 | Cross-linked Rubber | 0.1 to 50 |
| Reactive-Cyclic-based Adhesion Promoter | 0 | Ring-opening-based Adhesion Promoter | 5.0 to 50 |

TABLE 6

| Component A | Weight % | Component B | Weight % |
|---|---|---|---|
| Reactive-Cyclic-based Polymerizable Compound | 0 | Ring-opening-based Polymerizable Compound | 5.0 to 50 |
| Catalyst | 0 | Catalyst | 0.001 to 5.0 |
| Radiopacifier | 20 to 80 | Radiopacifier | 20 to 80 |
| Reinforcing Fillers | 0.1 to 25 | Reinforcing Fillers | 0.1 to 25 |
| Cross-linked Rubber | 0.1 to 50 | Cross-linked Rubber | 0.1 to 50 |
| Reactive-Cyclic-based Adhesion Promoter | 5.0 to 50 | Ring-opening-based Adhesion Promoter | 0 |

Desirably, the cyclic-based polymerizable compound and the cyclic-based adhesion promoter include epoxy functionality, while the ring opening-based polymerizable compound and the ring opening-based adhesion promoter include amine functionality, though not required. It is appreciated that in a composite sealant composition that includes an adhesion promoter as the polymerizable compound (Example of Table 7), the adhesion promoter may in an amount of at least about 1%, preferably at least about 5%, and more preferably at least about 10% by wt the overall composite sealant composition. Furthermore, it is appreciated that the adhesion promoter may be present in an amount of less than about 90%, preferably less than about 70% and preferably less than about 50% by wt the overall composite sealant composition. For example, the adhesion promoter may be present in an amount ranging from about 1% to about 90%, preferably from about 5% to about 70%, and more preferably from about 10% to about 50% by wt the overall composite sealant composition.

TABLE 7

| Component A | Weight % | Component B | Weight % |
|---|---|---|---|
| Reactive-Cyclic-based Adhesion Promoter | 5.0 to 50 | Ring-opening-based Adhesion Promoter | 5.0 to 50 |
| Catalyst | 0 | Catalyst | 0.001 to 5.0 |

TABLE 7-continued

| Component A | Weight % | Component B | Weight % |
|---|---|---|---|
| Radiopacifier | 20 to 80 | Radiopacifier | 20 to 80 |
| Reinforcing Fillers | 0.1 to 25 | Reinforcing Fillers | 0.1 to 25 |
| Cross-linked Rubber | 0.1 to 50 | Cross-linked Rubber | 0.1 to 50 |

Desirably, the cyclic-based adhesion promoter includes epoxy functionality, while the ring opening-based adhesion promoter includes amine functionality, though not required.

In one specific two-component example, the product may comprise of a putty formulation, which includes ground cross-linked material (e.g., ground cross-lined endodontic carriers), silica, polymer, catalyst and bismuth oxide. The formulation mixes into a firm putty which can be delivered with an amalgum delivery device or with pluggers and spreaders. It has the consistency of a putty and can be rolled into any desired shaped prior to placing into the canal. Once the canal is filled, a gutta-percha point or a cross-linked endodontic carrier can be inserted into the canal to facilitate a 3-d fill and prevent leakage out the apex.

In another specific example, the composite sealant composition may comprise of an injectable formulation which includes ground cross-linked material, silica, polymer, catalyst, and bismuth oxide. The formulation mixes in a static mixer connected on the end of a dual syringe. The material is directly injected into the canal. Once the canal is filled, a cross-linked endodontic carrier or gutta-percha-point can be inserted into the canal to facilitate a 3-d fill and prevent leakage out the apex.

It is appreciated that the gutta-percha point/cross-linked carrier choice can left up to the clinician (they are interchangeable).

It is further appreciated that in the composite sealant composition systems, different types can be used. The sealant material according to the invention can be present as single-component systems or as multi-component systems, preferably as two-component systems, as a function of the polymer system, in each instance. The curable polymer systems and their additional components, such as catalysts and/or initiators, are known to a person skilled in the art as such.

Preferably, one-component dental sealant materials are used that are cured by means of UV radiation and/or heat. Aside from the curable polymer system as well as the surfactant mixture used according to the invention, photoinitiators are usually contained in them It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein.

The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The invention claimed is:

1. An endodontic composite sealant composition for filling and sealing a root canal comprising an adhesion promoter, wherein the adhesion promoter is characterized by the following formula (I):

$$R^1\text{—}R^2\text{—}W\text{—}Z\text{—}R^3\text{—}R^4 \qquad (I)$$

wherein

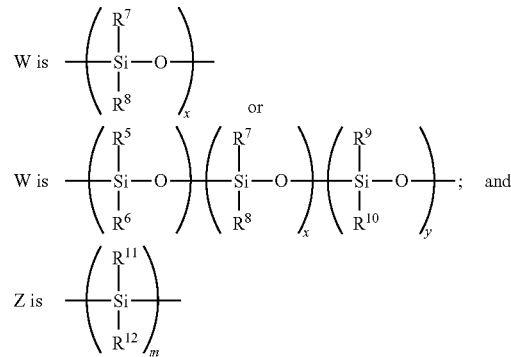

wherein

R$^1$ and R$^4$ are independently Hydrogen, NH$_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group;

R$^2$ and R$^3$ are independently a C$_{1-10}$ alkyl group, NH$_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group;

R$^5$, R$^6$, R$^7$, R$^8$, R$^9$, R$^{10}$, R$^{11}$, and R$^{12}$ are independently Hydrogen, a C$_{1-10}$ alkyl group, or a C$_{1-10}$—R$^{13}$ group such that R$^{13}$ is independently NH$_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group, whereas multiple groups of R$^5$, R$^6$, R$^7$, R$^8$, R$^9$, R$^{10}$, R$^{11}$, R$^{12}$, and R$^{13}$ may be identical or different; and x is an integer from 1 to 1000, multiple groups of x may be identical or different;

y is an integer from 1 to 1000, multiple groups of y may be identical or different; and m is an integer from 1 to 1000, multiple groups of m may be identical or different.

2. The composition of claim 1, wherein a portion of the adhesion promoter includes a ring-opening functionality, a reactive-cyclic functionality, a free radical functionality, or any combination thereof.

3. The composition of claim 1, wherein the adhesion promoter includes a dentin binding functionality.

4. The composition of claim 3, wherein the dentin binding functionality includes a negative charge, a positive charge, an amphoteric charge, or a zwitterionic charge.

5. The composition of claim 4, wherein the negative or positive charge comprises carboxylic acid groups, sulfate groups, amine groups, phosphate groups, quaternary ammonium groups and sulfonate, betaine, phosphatidylcholine groups.

6. The composition of claim 1, wherein:
i) $R^1$ and $R^4$ are independently an epoxide, a succunic anhydride, or a succinimide group;
ii) $R^1$ and $R^4$ are independently $NH_2$, OH, COOH, or SH group; or
iii) at least one of $R^1$ and $R^4$ is independently a phosphate, a sulfate, a sulfonate, a betaine, a carboxylic acid, an amino acid, a diacids, a bisphosphate, or a phosphatidylcholine group.

7. The composition of claim 1, wherein:
i) $R^1$ and $R^4$ are independently an epoxide, a succunic anhydride, or a succinimide group; and
ii) at least one of $R^5$, $R^6$, $R^7$, $R^8$, $R^9$, $R^{10}$, $R^{11}$, and $R^{12}$ is independently the $C_{1-10}$—$R^{13}$ group such that $R^{13}$ is independently the phosphate, the sulfate, the sulfonate, the betaine, the carboxylic acid, the amino acid, the diacids, the bisphosphate, or the phosphatidylcholine group.

8. The composition of claim 1, wherein:
i) $R^1$ and $R^4$ are independently $NH_2$, OH, COOH, or SH group; and
ii) at least one of $R^5$, $R^6$, $R^7$, $R^8$, $R^9$, $R^{10}$, $R^{11}$, and $R^{12}$ is independently the $C_{1-10}$—$R^{13}$ group such that $R^{13}$ is independently the phosphate, the sulfate, the sulfonate, the betaine, the carboxylic acid, the amino acid, the diacids, the bisphosphate, or the phosphatidylcholine group.

9. The composition of claim 1, wherein:
i) at least one of $R^1$ and $R^4$ is independently a phosphate, a sulfate, a sulfonate, a betaine, a carboxylic acid, an amino acid, a diacids, a bisphosphate, or a phosphatidylcholine group; and
ii) at least one of $R^5$, $R^6$, $R^7$, $R^8$, $R^9$, $R^{10}$, $R^{11}$, and $R^{12}$ is independently the $C_{1-10}$—$R^{13}$ group such that $R^{13}$ is independently the $NH_2$, OH, COOH, SH, epoxide, succunic anhydride, or succinimide group, whereas $NH_2$, OH, COOH, or SH group is not present when the epoxide, the succunic anhydride, or the succinimide group is present.

10. The composition of claim 1, wherein $R^5$, $R^6$, $R^{11}$, and $R^{12}$ are independently a $C_{1-10}$ alkyl group.

11. The composition of claim 1, wherein

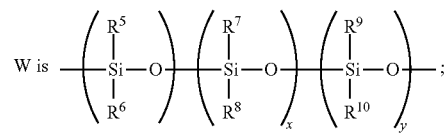

and
wherein
$R^1$ and $R^4$ are independently Hydrogen, a phosphate, a sulfate, a sulfonate, a betaine, a carboxylic acid, an amino acid, a diacids, a bisphosphate, or a phosphatidylcholine group, provided at least one of $R^1$ and $R^4$ is not Hydrogen;
$R^2$ and $R^3$ are independently a $C_{1-10}$ alkyl group; and
$R^5$, $R^6$, $R^7$, $R^8$, $R^9$, $R^{10}$, $R^{11}$, and $R^{12}$ are independently Hydrogen, a $C_{1-10}$ alkyl group, or a $C_{1-10}$—$R^{13}$ group such that $R^{13}$ is independently $NH_2$, OH, COOH, SH, an epoxide, a succunic anhydride, or a succinimide group, whereas multiple groups of $R^7$, $R^8$, $R^9$, $R^{10}$, $R^{11}$, $R^{12}$, and $R^{13}$ may be identical or different, provided at least two of $R^5$, $R^6$, $R^7$, $R^8$, $R^9$, $R^{10}$, $R^{11}$, and $R^{12}$ includes the $C_{1-10}$—$R^{13}$ group.

12. The composition according to claim 11, wherein $NH_2$, OH, COOH, or SH is not present when the epoxide, the succunic anhydride, or the succinimide group is present.

13. The composition of claim 11, wherein at least two of $R^5$, $R^6$, $R^7$, $R^8$, $R^9$, $R^{10}$, $R^{11}$, and $R^{12}$ includes the $C_{1-10}$—$R^{13}$ group.

14. The composition of claim 11, wherein x ranges from 1-50, y ranges from 25-250, and m is 1.

15. An endodontic composite sealant composition for filling and sealing a root canal comprising an adhesion promoter, wherein the adhesion promoter includes a first component and a second component,
a) the first component is characterized by the following formula (IIa):

$$R^1—R^2—W—Z—R^3—R^4 \quad \text{(IIa)};$$

wherein
$R^1$ and $R^4$ are independently $NH_2$, OH, COOH, or SH;
$R^2$ and $R^3$ are independently a $C_{1-10}$ alkyl group;

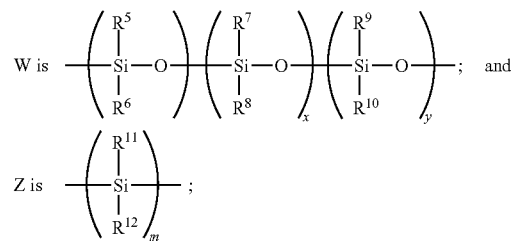

$R^5$, $R^6$, $R^7$, $R^8$, $R^9$, $R^{10}$, $R^{11}$ and $R^{12}$ are independently Hydrogen, a $C_{1-10}$ alkyl group, or a $C_{1-10}$—$R^{13}$ group such that $R^{13}$ is independently a phosphate, a sulfate, a sulfonate, a betaine, a carboxylic acid, an amino acid, a diacids, a bisphosphate, or a phosphatidylcholine group, whereas multiple groups of $R^5$, $R^6$, $R^7$, $R^8$, $R^9$, $R^{10}$, $R^{11}$, $R^{12}$, and $R^{13}$ may be identical or different;
x is an integer from 1 to 1000, multiple groups of x may be identical or different;
y is an integer from 1 to 1000, multiple groups of y may be identical or different; and m is an integer from 1 to 10, multiple groups of m may be identical or different; and b) the second component is characterized by the following formula (IIb):

$$R^{13}\text{—}R^{14}\text{—}W\text{—}Z\text{—}R^{15}\text{—}R^{16} \qquad (IIb);$$

wherein
$R^{13}$ and $R^{16}$ are independently an epoxide, a succunic anhydride, or a succinimide group;
$R^{14}$ and $R^{15}$ are independently a $C_{1-10}$ alkyl group;

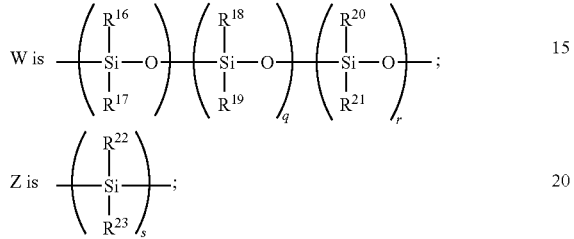

$R^{16}$, $R^{17}$, $R^{18}$, $R^{19}$, $R^{20}$, $R^{21}$, $R^{22}$, and $R^{23}$ are independently Hydrogen, a $C_{1-10}$ alkyl group, or a $C_{1-10}$—$R^{24}$ group such that $R^{24}$ is independently a phosphate, a sulfate, a sulfonate, a betaine, a carboxylic acid, an amino acid, a diacids, a bisphosphate, or a phosphatidylcholine group, whereas multiple groups of $R^{16}$, $R^{17}$, $R^{18}$, $R^{19}$, $R^{20}$, $R^{21}$, $R^{22}$, $R^{23}$, and $R^{24}$ may be identical or different;
q is an integer from 1 to 1000, multiple groups of q may be identical or different;
r is an integer from 1 to 1000, multiple groups of r may be identical or different; and
s is an integer from 1 to 10, multiple groups of s may be identical or different.

16. The composition of claim 15, wherein
i) at least one of $R^5$, $R^6$, $R^7$, $R^8$, $R^9$, $R^{10}$, $R^{11}$, $R^{12}$ includes the $C_{1-10}$—$R^{13}$ group; and/or
ii) at least one of $R^{16}$, $R^{17}$, $R^{18}$, $R^{19}$, $R^{20}$, $R^{21}$, $R^{22}$, and $R^{23}$ includes the $C_{1-10}$—$R^{24}$ group.

17. The composition of claim 15, wherein
i) at least one of $R^7$ and $R^8$ includes the $C_{1-10}$—$R^{13}$ group; and/or
ii) at least one of $R^{18}$ and $R^{19}$ includes the $C_{1-10}$—$R^{24}$ group.

18. The composition of claim 15, wherein x ranges from 1-50, y ranges from 25-250, and m is 1 and wherein q ranges from 1-50, r ranges from 25-250, and s is 1.

19. An endodontic composite sealant composition for filling and sealing a root canal comprising an adhesion promoter, wherein the adhesion promoter includes a first component and a second component,
a) the first component is characterized by the following formula (IIIa):

$$R^1\text{—}R^2\text{—}W\text{—}Z\text{—}R^3\text{—}R^4 \qquad (IIIa);$$

wherein
$R^1$ and $R^4$ are independently Hydrogen, a phosphate, a sulfate, a sulfonate, a betaine, a carboxylic acid, an amino acid, a diacids, a bisphosphate, or a phosphatidylcholine group, provided at least one of $R^1$ and $R^4$ is not Hydrogen;
$R^2$ and $R^3$ are independently a substituted or unsubstituted $C_{1-10}$ alkyl group;

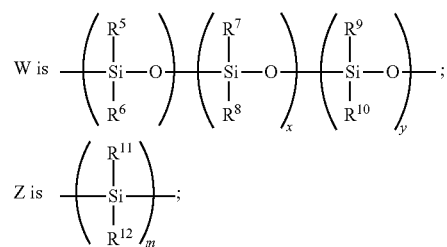

$R^5$, $R^6$, $R^7$, $R^8$, $R^9$, $R^{10}$, $R^{11}$ and $R^{12}$ are independently Hydrogen, a $C_{1-10}$ alkyl group, or a $C_{1-10}$—$R^{13}$ group such that $R^{13}$ is independently $NH_2$, OH, COOH, SH, whereas multiple groups of $R^7$, $R^8$, $R^9$, $R^{10}$, $R^{11}$, $R^{12}$, and $R^{13}$ may be identical or different;
x is an integer from 1 to 1000, multiple groups of x may be identical or different;
y is an integer from 1 to 1000, multiple groups of y may be identical or different; and
m is an integer from 1 to 10, multiple groups of m may be identical or different; and b) the second component is characterized by the following formula (IIIb):

$$R^{13}\text{—}R^{14}\text{—}W\text{—}Z\text{—}R^{15}\text{—}R^{16} \qquad (IIIb);$$

wherein
$R^{13}$ and $R^{16}$ are independently Hydrogen, a phosphate, a sulfate, a sulfonate, a betaine, a carboxylic acid, an amino acid, a diacids, a bisphosphate, or a phosphatidylcholine group, provided at least one of $R^1$ and $R^4$ is not Hydrogen;
$R^{14}$ and $R^{15}$ are independently a substituted or unsubstituted $C_{1-10}$ alkyl group;

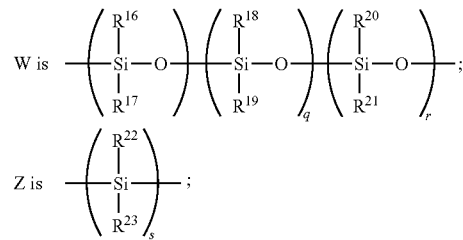

$R^{16}$, $R^{17}$, $R^{18}$, $R^{19}$, $R^{20}$, $R^{21}$, $R^{22}$, and $R^{23}$ are independently Hydrogen, a $C_{1-10}$ alkyl group, or a $C_{1-10}$—$R^{24}$ group such that $R^{24}$ is independently an epoxide, a succunic anhydride, or a succinimide group, whereas multiple groups of $R^{16}$, $R^{17}$, $R^{18}$, $R^{19}$, $R^{20}$, $R^{21}$, $R^{22}$, $R^{23}$, and $R^{24}$ may be identical or different;
q is an integer from 1 to 1000, multiple groups of q may be identical or different;
r is an integer from 1 to 1000, multiple groups of r may be identical or different; and
s is an integer from 1 to 10, multiple groups of s may be identical or different.

20. The composition of claim 19, wherein
i) at least one of $R^5$, $R^6$, $R^7$, $R^8$, $R^9$, $R^{10}$, $R^{11}$, $R^{12}$ includes the $C_{1-10}$—$R^{13}$ group; and/or
ii) at least one of $R^{16}$, $R^{17}$, $R^{18}$, $R^{19}$, $R^{20}$, $R^{21}$, $R^{22}$, and $R^{23}$ includes the $C_{1-10}$—$R^{24}$ group.

21. The composition of claim 19, wherein x ranges from 1-50, y ranges from 25-250, and m is 1; and wherein q ranges from 1-50, r ranges from 25-250, and s is 1.

22. An endodontic composite sealant composition for filling and sealing a root canal comprising an adhesion promoter, wherein adhesion promoter is characterized by the following formula (IV):

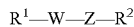
(IV)

wherein
$R^1$ and $R^2$ are independently a substituted or unsubstituted $C_{1-11}$ alkyl group;

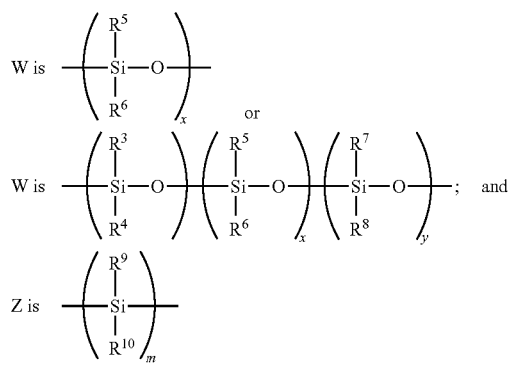

wherein
$R^3$, $R^4$, $R^5$, $R^6$, $R^7$, $R^8$, $R^9$, and $R^{10}$ are independently Hydrogen, a $C_{1-10}$ alkyl group, or a $C_{1-10}$—$R^{11}$ group such that $R^{11}$ is independently $NH_2$, OH, COOH, SH, an epoxide, a succunic anhydride, a succinimide group, a phosphate, a sulfate, a sulfonate, a betaine, a carboxylic acid, an amino acid, a diacids, a bisphosphate, or a phosphatidylcholine group; whereas multiple groups of $R^3$, $R^4$, $R^5$, $R^6$, $R^7$, $R^8$, $R^9$, $R^{10}$, and $R^{11}$ may be identical or different; provided that at least one of $R^3$, $R^4$ $R^5$, $R^6$, $R^7$, and $R^8$ includes the $C_{1-10}$—$R^{11}$ group;
x is an integer from 1 to 1000, multiple groups of x may be identical or different;
y is an integer from 1 to 1000, multiple groups of y may be identical or different; and
m is an integer from 1 to 10, multiple groups of m may be identical or different.

23. The composition according to claim 22, wherein $NH_2$, OH, COOH, or SH is not present when the epoxide, the succunic anhydride, or the succinimide group is present.

24. The composition of claim 22, wherein

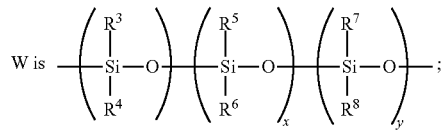

and
wherein
$R^3$, $R^4$, $R^7$, $R^8$, $R^9$, $R^{10}$, and $R^{11}$ include the $C_{1-10}$ alkyl group;
x ranges from 1-50;
y ranges from 25-250; and
m is 1.

25. An endodontic composite sealant composition for filling and sealing a root canal comprising an adhesion promoter, wherein the adhesion promoter includes a first component and a second component,
a) the first component is characterized by the following formula (IVa):

(IVa)

wherein
$R^1$ and $R^2$ are independently a substituted or unsubstituted $C_{1-11}$ alkyl group;

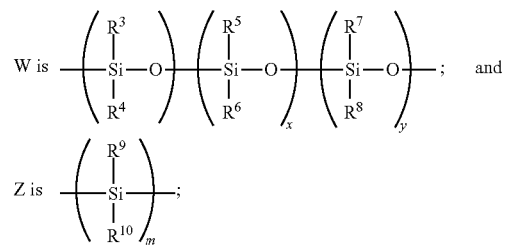

wherein
$R^3$, $R^4$, $R^5$, $R^6$, $R^7$, $R^8$, $R^9$, and $R^{10}$ are independently Hydrogen, a $C_{1-10}$ alkyl group, or a $C_{1-10}$—$R^{11}$ group such that $R^{11}$ is independently $NH_2$, OH, COOH, or SH; whereas multiple groups of $R^3$, $R^4$, $R^5$, $R^6$, $R^7$, $R^8$, $R^9$, $R^{10}$, and $R^{11}$ may be identical or different; provided that at least one of $R^3$, $R^4$ $R^5$, $R^6$, $R^7$, and $R^8$ includes the $C_{1-10}$—$R^{11}$ group;
x is an integer from 1 to 1000, multiple groups of x may be identical or different;
y is an integer from 1 to 1000, multiple groups of y may be identical or different; and
m is an integer from 1 to 10, multiple groups of m may be identical or different; and
b) the second component is characterized by the following formula (IVb):

(IVb)

wherein
$R^{12}$ and $R^{13}$ are independently a substituted or unsubstituted $C_{1-11}$ alkyl group;

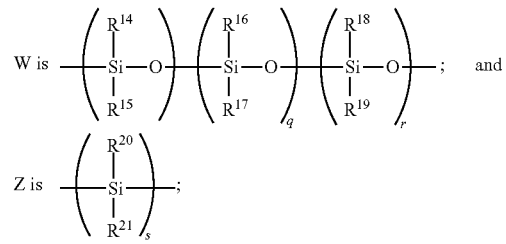

wherein
$R^{14}$, $R^{15}$, $R^{16}$, $R^{17}$, $R^{18}$, $R^{19}$, $R^{20}$, and $R^{21}$ are independently Hydrogen, a $C_{1-10}$ alkyl group, or a $C_{1-10}$—$R^{22}$ group such that $R^{22}$ is independently an epoxide, a succunic anhydride, or a succinimide group; whereas multiple groups of $R^{14}$, $R^{15}$, $R^{16}$, $R^{17}$, $R^{18}$, $R^{19}$, $R^{20}$, $R^{21}$, and $R^{22}$ may be identical or different; provided that at least one of $R^{14}$, $R^{15}$, $R^{16}$, $R^{17}$, $R^{18}$, and $R^{19}$ includes the $C_{1-10}$—$R^{11}$ group;
q is an integer from 1 to 1000, multiple groups of x may be identical or different;

r is an integer from 1 to 1000, multiple groups of y may be identical or different; and s is an integer from 1 to 10, multiple groups of m may be identical or different.

26. The composition of claim 25, wherein
i) at least one of $R^5$, $R^6$, $R^7$, and $R^8$ includes the $C_{1-10}$—$R^{11}$ group; and
ii) at least one of $R^{16}$, $R^{17}$, $R^{18}$, and $R^{19}$ includes the $C_{1-10}$—$R^{22}$ group.

27. The composition of claim 25, wherein x ranges from 1-50, y ranges from 25-250, and m is 1; and wherein q ranges from 1-50, r ranges from 25-250, and s is 1.

28. The composition of claim 25, wherein
i) at least one of $R^5$, $R^6$, $R^7$, and $R^8$ is independently a $C_{1-10}$—$R^{23}$ group such that $R^{23}$ is a phosphate, a sulfate, a sulfonate, a betaine, a carboxylic acid, an amino acid, a diacids, a bisphosphate, or a phosphatidylcholine group; whereas multiple groups of $R^5$, $R^6$, $R^7$, and $R^8$ may be identical or different; and/or
ii) at least one of $R^{16}$, $R^{17}$, $R^{18}$, and $R^{19}$ is independently a $C_{1-10}$—$R^{24}$ group such that $R^{24}$ is a phosphate, a sulfate, a sulfonate, a betaine, a carboxylic acid, an amino acid, a diacids, a bisphosphate, or a phosphatidylcholine group; whereas multiple groups of $R^{16}$, $R^{17}$, $R^{18}$, and $R^{19}$ may be identical or different.

29. The composition of claim 1, further comprising bioglass or a bioactive glass.

30. The composition of claim 15, wherein the first component, the second component or both further include bioglass or a bioactive glass.

31. The composition of claim 19, wherein the first component, the second component or both further include bioglass or a bioactive glass.

32. The composition of claim 22, further comprising bioglass or a bioactive glass.

33. The composition of claim 25, wherein the first component, the second component or both further include bioglass or a bioactive glass.

* * * * *